US006346229B1

(12) United States Patent
Driehuys et al.

(10) Patent No.: US 6,346,229 B1
(45) Date of Patent: Feb. 12, 2002

(54) METHODS FOR IMAGING PULMONARY AND CARDIAC VASCULATURE AND EVALUATING BLOOD FLOW USING DISSOLVED POLARIZED $^{129}$XE

(75) Inventors: Bastiaan Driehuys; Kenton Christopher Hasson, both of Durham; Paul Lev Bogorad, Hillsborough, all of NC (US)

(73) Assignee: Medi-Physics, Inc., Princeton, NJ (US)

( * ) Notice: Subject to any disclaimer, the term of this patent is extended or adjusted under 35 U.S.C. 154(b) by 0 days.

(21) Appl. No.: 09/271,476

(22) Filed: Mar. 17, 1999

Related U.S. Application Data

(63) Continuation of application No. 09/271,476, filed on Mar. 17, 1999.
(60) Provisional application No. 60/078,384, filed on Mar. 18, 1998.

(51) Int. Cl.$^7$ .............................................. A61B 5/055

(52) U.S. Cl. ......................... 424/9.36; 424/9.1; 424/9.3

(58) Field of Search ........................ 424/9.1, 9.3, 9.32, 424/9.36

(56) References Cited

U.S. PATENT DOCUMENTS

| | | | |
|---|---|---|---|
| 4,586,511 A | 5/1986 | Clark, Jr. ..................... | 128/653 |
| 5,190,744 A | 3/1993 | Rocklage et al. .............. | 424/9 |
| 5,352,979 A | 10/1994 | Conturo ....................... | 324/307 |
| 5,494,655 A | 2/1996 | Rocklage et al. ........... | 424/9.36 |
| 5,509,412 A | 4/1996 | Bahn ........................ | 128/653.2 |
| 5,522,390 A | 6/1996 | Tuithof et al. ............ | 128/653.2 |
| 5,545,396 A | 8/1996 | Albert et al. ................. | 424/93 |
| 5,617,860 A | 4/1997 | Chupp et al. ............. | 128/653.4 |
| 5,642,625 A | 7/1997 | Cates, Jr. et al. ............ | 62/55.5 |
| 5,809,801 A | 9/1998 | Cates, Jr. et al. ............. | 62/637 |
| 5,833,947 A | 11/1998 | Rocklage et al. .......... | 424/9.36 |
| 5,936,404 A | 8/1999 | Ladebeck et al. ........... | 324/300 |

FOREIGN PATENT DOCUMENTS

| | | |
|---|---|---|
| WO | WO95/27438 | 2/1995 |
| WO | WO 98/58272 | 12/1998 |
| WO | WO 99/07415 | 2/1999 |
| WO | WO 99/14582 | 3/1999 |

OTHER PUBLICATIONS

Il'yasov et al., "$^{129}$Xe NMR in Study of Tissues and Plants," Appl. Magn. Reson. vol. 17, pp. 77–84 (1999).
Mazitov et al. "NMR Spectroscopy of $^{129}$Xe Dissolved in Tissues of Animals and Plants in vitro: Effect of Tissue with Cancer," Doklady Biophysics, vols. 364–366, pp. 28–31 (1999); translated from Doklady Akademii Nauk, vol. 365, No. 3 pp. 396–399 (1999).
Albert et al., "Development of hyperpolarized noble gas MRI," Nucl. Inst. and Meth. in Phys. Res. A 402, pp. 441–453 (1998).
Albert, "Measurement of $^{129}$Xe T1 in blood to explore the feasibility of hyperpolarized $^{129}$Xe MRI," Jour. Comp. Ass. Tomography, vol. 19, No. 6 (Nov.–Dec. 1995).
Augustine et al, "Low field magnetic resonance images of polarized noble gases obtained with a dc superconducting quantum interference device," App. Phys. Ltrs, vol. 72, No. 15, pp. 1908–1910 (Apr. 1998).
Belliveau et al., "Functional Cerebral Imaging by Susceptibility–Contrast NMR," 14 Magnetic Resonance in Medicine 14, pp. 538–546 (1990).
Bifone et al., "NMR of laser–polarized xenon in human blood," 93 Proc. Natl. Acad. Sci. USA, vol. 93, p. 12932–12935 (Nov. 1996).
Bishop et al., "High–Order Multipolar Hyperpolarizabilities with Imaginary Frequency for H and He," Int'l Jour. of Quan. Chem., vol. 59, pp. 103–108 (1996).
Black et al. "In Vivo He–3 MR Images of Guinea Pigs Lungs[1]," Radiology, vol. 199, No. 3, pp. 867–870 (Jun. 1996).
Bock, "Simultaneous $T_2$* and Diffusion Measurements with $^3$He," Mag. Reson. in Med., vol. 38, No. 6, pp. 890–895 (1997).
Borman, Xenon used to expand magnetic imaging, Chem. & Eng. News, vol. 72, No. 30, pp. 7–8 (Jul. 25, 1994).
Chen et al., "MR Microscopy of Lung Airways with Hyperpolarized $^3$He," Mag. Reson. in Med., vol. 39, No. 1, pp. 79–84 (Jan. 1998).
Constantinesco et al., "MRI of hyperpolarized gases in competition with nuclear medicine?", Médecine Nucléaire, vol. 21, No. 5, pp. 285–292 (1997–98).
Detre et al., "Measurement of Regional Cerebral Blood Flow in Cat Brain Using Intracartoid $^2H_2O$ and $^2H$ NMR Imaging," 14 Mag. Reson. in Med., p. 389–395 (1990).
Ebert et al., "Nuclear magnetic resonance imaging with hyperpolarised helium–3," Lancet (NA ed), vol. 347, pp. 1297–1299 (May 1996).
Frank et al., "Dynamic Dysprosium–DTPA–BMA Enhanced MRI of the Occipital Cortex; Functional Imaging in Visually Impaired Monkeys by PET and MRI" (Abstract), Ninth Annual Scientific Meeting and Exhibition of the Society of Magnetic Resonance in Medicine (Aug. 18–24), 1990.
Gao et al., "Magnetization and Diffusion Effects in NMR Imaging of Hyperpolarized Substances," Mag. Reson. in Med., vol. 37, No. 1, pp. 153–158 (Jan. 1997).

*Primary Examiner*—Dameron Jones
(74) *Attorney, Agent, or Firm*—Myers Bigel Sibley & Sajovec, P.A.

(57) ABSTRACT

MR spectroscopy and imaging method for imaging pulmonary and cardiac vasculature and the cardiac region and evaluating blood flow or circulatory deficits use dissolved phase polarized $^{129}$Xe gas and large flip angle excitation pulses. Pulmonary and cardiac vasculature MRI images are obtained by delivering gas to a patient via inhalation such as with a breath-hold delivery-procedure, exciting the dissolved phase gas with a large flip angle pulse, and generating a corresponding image. Preferably, the image is obtained using multi-echo imaging techniques. Blood flow is quantified using low field MR spectroscopy and an RF excitation pulse with a frequency which corresponds to the resonance of the dissolved phase $^{129}$Xe.

52 Claims, 4 Drawing Sheets

OTHER PUBLICATIONS

George, "The Sharper Image: MRIs and Xenon Gas," Jour. of NIH Res., vol. 6, No. 12, pp. 42–44 (Dec. 1994).

Glover et al., Research Directions in MR Imaging[1], Radiology., vol. 207, pp. 289–295, (1988).

Hardy et al., "Broadband nuclear magnetic resonance pulses with two–dimensional spatial selectivity," J. Appl. Phys., vol. 66, No. 4, pp. 1513–1516 (Aug. 15, 1989).

Hardy et al., "Correcting for Nonuniform k–Space Sampling in Two–Dimensional NMR Selective Excitation," Jnl. Magnetic Resonance, vol. 87, pp. 639–645 (1990).

Hardy et al., "Spatial Localization in Two Dimensions Using NMR Designer Pulses," Jnl. Magnetic Resonance, vol. 82, pp. 647–654 (1989).

Heil et al., "Very long nuclear relaxation times of spin polarized helium 3 in metal coated cells," Physics Letters A 201, pp. 337–343 (1995).

Hou et al., "Optimization of Fast Acquisition Methods for Whole–Brain Relative Cerebral Blood Volume (rCBV) Mapping with Susceptibility Contrast Agents," 9 J. Mag. Reson. Imag., 233–239 (1999).

Kauczor et al., "MRI Using Hyperpolarized Noble Gases," Eur. Radiol., vol. 8, No. 5, Abstract (1998).

Kauczor et al., "Normal and Abnormal Pulmonary Ventilation: Visualization of Hyperpolarized He–3 MR Imaging[1]," Radiology, vol. 201, No. 2, pp. 564–568 (1996).

Lassen, "Cerebral Transit of an Intravascular Tracer May Allow Measurement of Regional Blood Volume But Not Regional Blood Flow," 4 J. Cereb. Blood Flow and Metab. pp. 633–634 (1984).

Le Bihan, "Magnetic Resonance Imaging of Perfusion*," Mag. Reson. in Med., vol. 14, pp. 283–292 (1990).

MacFall et al., "Human Lung Air Spaces: Potential for MR Imaging with Hyperpolarized He–3[1]," Radiology, vol. 200, No. 2, pp. 553–558 (1996).

Martin, "The Pharmacokinetics of Hyperpolarized Xenon: Implications for Cerebral MRI,"0 Jour. Magn. Reson. Imag., vol. 7, No. 5, pp. 848–854, (Sep.–Oct. 1997).

Middleton et al., "MR Imaging With Hyperpolarized $^3$He Gas", Magnetic Resonance In Medicine, vol. 33, pp. 271–275 (1995).

Mugler, III et al. Gradient–Echo MR Imaging, RSNA Categorical Course in Physics: The Basic Physics of MR Imaging[1], U. of VA Health Sci. Ctr., pp. 71–88 (1997).

Mugler, III et al., "MR Imaging and Spectroscopy Using Hyperpolarized 129Xe Gas: Preliminary Human Results," 37 Magn. Reson. in Med., vol. 37, No. 6, pp. 809–815 (1997).

Pennisi, Breathe (xenon) deeply to see lungs clearly, Sci. News, vol. 146, p. 70.

Pfeffer et al., "$^{129}$Xe gas NMR spectroscopy and imaging with a whole–body imager," J. Mag. Reson., Ser. A., vol. 108, No. 1, pp. 106–109 (May 1994).

Rinck et al., "NMR–Imaging of Fluorine–Containing Substances 19–Fluorine Ventilation and Perfusion Studies!", vol. 140, No. 3, pp. 239–243 (Mar. 1984).

Rosen et al., "Perfusion Imaging by Nuclear Magnetic Resonance," Mag. Reson. Quart., vol. 5, No. 4, pp. 263–281 (1989).

Schmidt et al., "Diffusion Imaging with Hyperpolarized $^3$He Gas," Jour. Mag. Reson., vol. 129, pp. 184–187 (1997).

Simonsen et al., "CBF and CBV Measurements by USPIO Bolus Tracking: Reproducibility and Comparison with Gd–Based Values," J. of Mag. Reson. Imag., vol. 9, pp. 342–347 (1999).

Sled et al., "Standing–Wave and RF Penetration Artifacts Caused by Elliptic Geometry: An Electrodynamic Analysis of MRI," IEEE Transactions on Medical Imaging, vol. 17, No. 4, pp. 653–662 (Aug. 1998).

Song et al., "Effects of Diffusion on Magnetic Resonance Imaging of Laser–Polarized Xenon Gas," Jour. Chem. Phys., vol. 108, No. 15, pp. 6233–6239 (Apr. 1998).

Wagshul, "*In Vivo* MR Imaging and Spectroscopy Using Hyperpolarized 129Xe," Mag. Reson. Med., vol. 36, No. 2, pp. 183–191 (Aug. 1996).

Darrasse, et al., "Low–field $^3$He nuclear magnetic resonance in human lungs," C.R. Acad. Sci., Paris, t. 324, Serie II b, pp. 691–700 (1997) (French).

De Schepper, "The HERMES $^3$He target," AIP conf. Proc., vol. 421, No. 1, pp. 16–25 (Jan. 1998).

Zhao, et al., "Biomedical imaging using hyperpolarized noble gas MRI: Pulse sequence considerations," Nuclear Instru. and Methods in Phys. Res. A 402, pp. 454–460 (1998).

PCT International Search Report, Int'l. Application No. PCT/US99/05788 dated Aug. 24, 1999.

METHODS FOR IMAGING PULMONARY AND CARDIAC VASCULATURE AND EVALUATING BLOOD FLOW USING DISSOLVED POLARIZED $^{129}$XE

RELATED APPLICATIONS

This application is a 37 CFR § 1.114 continuation of U.S. Patent Application Ser. No. 09/271,476, filed Mar. 17, 1999, which claims the benefit of priority from Provisional Application Ser. No. 60/078,384 filed Mar. 18, 1998.

GOVERNMENT GRANT INFORMATION

This invention was made with Government support under U.S. Air Force Grant number F41624-97-C-9001. The United States Government has certain rights in this invention.

FIELD OF THE INVENTION

The present invention relates to magnetic resonance imaging ("MRI") and MR spectroscopy using hyperpolarized noble gases. More particularly, the present invention relates to imaging techniques using dissolved phase noble gases.

BACKGROUND OF THE INVENTION

Conventionally, MRI has been used to produce images by exciting the nuclei of hydrogen molecules (present in water protons) in the human body. However, it has recently been discovered that polarized noble gases can produce improved images of certain areas and regions of the body which have heretofore produced less than satisfactory images in this modality. Polarized Helium 3 ("$^3$He") and Xenon-129 ("$^{129}$Xe") have been found to be particularly suited for this purpose. See U.S. Pat. No. 5,545,396 to Albert et al., entitled "Magnetic Resonance Imaging Using Hyperpolarized Noble Gases", the disclosure of which is hereby incorporated by reference herein as if recited in full herein.

In order to obtain sufficient quantities of the polarized gases necessary for imaging, hyperpolarizers are used to produce and accumulate polarized noble gases. Hyperpolarizers artificially enhance the polarization of certain noble gas nuclei (such as $^{129}$Xe or $^3$He) over the natural or equilibrium levels, i.e., the Boltzmann polarization. Such an increase is desirable because it enhances and increases the Magnetic Resonance Imaging ("MRI") signal intensity, thereby potentially allowing physicians to obtain better images of many tissues and organs in the body.

Generally stated, in order to produce the hyperpolarized gas, the hyperpolarizer is configured such that the noble gas is blended with optically pumped alkali metal vapors such as rubidium ("Rb"). These optically pumped metal vapors collide with the nuclei of the noble gas and hyperpolarize the noble gas through a phenomenon known as "spin-exchange". The "optical pumping" of the alkali metal vapor is produced by irradiating the alkali-metal vapor with circularly polarized light at the wavelength of the first principal resonance for the alkali metal (e.g., 795 nm for Rb). Generally described, the ground state atoms become excited, then subsequently decay back to the ground state. Under a modest magnetic field (10 Gauss), the cycling of atoms between the ground and excited states can yield nearly 100% polarization of the atoms in a few microseconds. This polarization is generally carried by the lone valence electron characteristics of the alkali metal. In the presence of non-zero nuclear spin noble gases, the alkali-metal vapor atoms can collide with the noble gas atoms in a manner in which the polarization of the valence electrons is transferred to the noble-gas nuclei through a mutual spin flip "spin-exchange".

Conventionally, lasers have been used to optically pump the alkali metals. Various lasers emit light signals over various wavelength bands. In order to improve the optical pumping process for certain types of lasers (particularly those with broader bandwidth emissions), the absorption or resonance line width of the alkali metal can be broadened to more closely correspond with the particular laser emission bandwidth of the selected laser. This broadening can be achieved by pressure broadening, i.e., by using a buffer gas in the optical pumping chamber. Collisions of the alkali metal vapor with a buffer gas can lead to a broadening of the alkali's absorption bandwidth.

For example, it is known that the amount of polarized $^{129}$Xe which can be produced per unit time is directly proportional to the light power absorbed by the Rb vapor. Thus, polarizing $^{129}$Xe in large quantities generally takes a large amount of laser power. When using a diode laser array, the natural Rb absorption line bandwidth is typically many times narrower than the laser emission bandwidth. The Rb absorption range can be increased by using a buffer gas. Of course, the selection of a buffer gas can also undesirably impact the Rb-noble gas spin-exchange by potentially introducing an angular momentum loss of the alkali metal to the buffer gas rather than to the noble gas as desired. In any event, after the spin-exchange has been completed, the hyperpolarized gas is separated from the alkali metal prior to introduction into a patient.

Conventionally, gas-phase imaging has been possible using both $^3$He and $^{129}$Xe, and has been particularly useful in producing ventilation-driven images of the lungs, a region where proton images have produced signal voids. However, in contrast to gas phase imaging, dissolved phase imaging has proven to be problematic. Dissolved phase imaging uses the solubility characteristic of $^{129}$Xe in blood and lipid rich tissue. The gas phase is thus absorbed or "dissolved" into surrounding tissue or blood vessels and may allow perfusion imaging of the brain, lung, or other regions. Such images can potentially allow for the performance of non-invasive studies of the pulmonary vasculature to detect emboli and other circulatory system problems. Unfortunately, once the polarized gas has been dissolved (such as into the blood vessels), it has proven difficult to generate clinically useful images using the dissolved phase gas. Conventionally, dissolved phase imaging is attempted by performing a gas-based "regular" image and then looking for a spatially shifted dissolved phase image. However, the small flip angles typically associated with the "regular" image excitation pulses generally fail to produce sufficient detectable signal spectra in the dissolved phase, thus generating relatively inadequate dissolved phase images.

For example, MRI images using gas-space-imaging techniques have been generated using hyperpolarized $^{129}$Xe gas. See Mugler III et al., *MR Imaging and Spectroscopy Using Hyperpolarized $^{129}$Xe gas: Preliminary Human Results*, 37 Magnetic Resonance in Medicine, pp. 809–815 (1997). While good correlation is seen between the gas-space signal in the xenon images and the gas-space signal void in the proton images, the spectra associated with the dissolved phase signal components were significantly lower than the gas-phase signal.

In addition, conventional imaging with MRI units generally requires relatively large magnetic fields. For example, 1.5 Tesla ("T") units are common. The large magnetic fields can require special housing and shielding within the use site.

Further, the MRI units must typically shim or control the magnetic field in order to produce magnet homogeneity which is suitable for imaging. As noted above, high field strength magnets generally require special handling and have relatively high operating costs. Unfortunately and disadvantageously, both the high field strength magnet and the relatively high homogeneity requirements can increase the unit's cost both to the medical facility and ultimately, the consumer.

OBJECTS AND SUMMARY OF THE INVENTION

In view of the foregoing, it is an object of the present invention to detect and/or manipulate dissolved-phase $^{129}$Xe signals in a manner that yields clinically useful images.

It is another object of the present invention to provide an imaging method which can obtain useful images of dissolved $^{129}$Xe in the pulmonary and/or cardiac vasculature.

It is an additional object of the present invention to provide an imaging method which yields useful images of the heart and major cardiac vessels using dissolved polarized $^{129}$Xe.

It is yet another object of the present invention to provide an imaging method which can obtain useful information and/or images of dissolved $^{129}$Xe which does not require high magnetic field strength and/or high magnetic field homogeneity.

It is a further object of the present invention to be able to obtain real-time blood flow path information such as local perfusion variation or blood flow abnormality using MR spectroscopy.

It is yet a further object of the present invention to provide an imaging method which can be used to determine quantitative measures of perfusion using dissolved polarized $^{129}$Xe.

These and other objects are satisfied by the present invention, which uses large flip angle (such as 90°) RF excitation pulses to excite dissolved phase gas in the pulmonary vasculature and MR data image acquisition techniques. In particular, a first aspect of the invention is directed to a method for obtaining MRI images using dissolved polarized $^{129}$Xe. The method includes positioning a patient in an MRI apparatus having a magnetic field associated therewith. Polarized $^{129}$Xe gas is delivered to the pulmonary region of the patient's body. Preferably, the $^{129}$Xe is inhaled and, due to the relatively high solubility of $^{129}$Xe, in a relatively short period of time, the inhaled polarized $^{129}$Xe gas enters into the body in the lung air spaces and either exists in the lung space as a gas and/or a gas which dissolves into adjacent vasculature, tissues, spaces, or organs. Thus, the solubility of polarized $^{129}$Xe in the body is such that it generates an associated hyperpolarized gas imaging phase and a hyperpolarized dissolved imaging phase. A predetermined region (i.e., a region of interest) of the patient's body which has a portion of the dissolved phase polarized gas therein is excited with a large angle (e.g. 90 degree) excitation pulse. At least one MRI image associated with the dissolved phase polarized gas is acquired after the excitation pulse. In a preferred embodiment, a multi-echo pulse sequence is used to generate an MR image. Further preferably, the excitation step is repeated within a predetermined repetition time. It is also preferred that the exciting step is performed so that the large angle pulse selectively excites substantially only the dissolved phase of the $^{129}$Xe.

Another aspect of the present invention is a method for evaluating (e.g., measuring, determining, quantifying, observing, monitoring, imaging and/or assessing) the blood flow of a patient. A patient or subject having a pulmonary and cardiac vasculature is positioned in a MR (magnetic resonance) spectroscopy system. Polarized gaseous $^{129}$Xe is delivered to the patient or subject. The pulmonary and cardiac vasculature has an associated blood flow path and a portion of the polarized gaseous $^{129}$Xe is dissolved into the pulmonary (and/or cardiac) vasculature blood flow path. The blood flow of the subject can be evaluated (to determine, e.g., xenon enhanced perfusion deficits, blood flow rate, blood volume, or blood flow path blockage) based on the spectroscopic signal of the dissolved $^{129}$Xe in the pulmonary (and/or cardiac) vasculature (i.e., a portion of the circulatory system's blood flow path between and including at least portions of the lungs and heart). Preferably the evaluating step includes a measuring step and blood flow path blockage can be detected by comparing the blood flow rates of healthy subjects with the subject's measured flow rate.

An additional aspect of the present invention is directed toward a cardiac imaging method. The method includes positioning a subject in an MRI system and delivering polarized $^{129}$Xe thereto. At least a portion of the polarized $^{129}$Xe is dissolved into the cardiac blood flow path of the subject. The dissolved polarized $^{129}$Xe is excited with a large angle RF excitation pulse and a MR image associated with the excited dissolved polarized $^{129}$Xe is generated. Preferably, the excitation pulse is selectively delivered to a target area along the cardiac blood flow path and is spatially limited to limit the depolarizing affect on the polarized gaseous $^{129}$Xe outside the target region.

Advantageously, unlike imaging the gas-phase $^{129}$Xe in the lung where conventionally small flip angles are used to avoid destroying the available $^{129}$Xe magnetization, there is minimal or no penalty for using a large flip angle excitation of the dissolved phase $^{129}$Xe because it will otherwise flow out of the chest region un-imaged. Indeed, a rapid large angle (such as 90 degree) pulse imaging sequence makes optimal use of the dissolved magnetization. The excitation repetition rate should be fast enough to capture the $^{129}$Xe before it flows out of the chest region. Such an imaging method can provide useful two (2) and three (3) dimensional dissolved phase images of the pulmonary and cardiac vasculature, images of anatomical features along the cardiac blood flow path, and patient blood flow rates and potential defects in the structure along the blood flow path of interest.

Further advantageously, blood flow abnormalities, perfusion variations (deficits or increases) and blood flow rate evaluation methods in spectroscopic systems according to the instant invention can be used in MRI units with reduced magnetic fields (such as 0.15 Tesla) and less restrictive homogeneity requirements. Further, the instant invention can use spectroscopic or MRI imaging techniques to obtain signal data corresponding to a quantity of dissolved polarized $^{129}$Xe before and after a physiologically active substance is administered to a human or animal body to evaluate the efficacy of the drug treatment or to quantitatively analyze a subject's blood flow.

The foregoing and other objects and aspects of the present invention are explained in detail herein.

DETAILED DESCRIPTION OF THE PREFERRED EMBODIMENTS

The present invention will now be described more fully hereinafter with reference to the accompanying figures, in which preferred embodiments of the invention are shown. This invention may, however, be embodied in many different forms and should not be construed as limited to the embodiments set forth herein. Like numbers refer to like elements throughout. Layers and regions may be exaggerated for clarity.

As known to those of skill in the art, polarized gases are collected, frozen, thawed, and used in MRI applications. For ease of description, the term "frozen polarized gas" means that the polarized gas has been frozen into a solid state. The term "liquid polarized gas" means that the polarized gas has been or is being liquefied into a liquid state. Thus, although each term includes the word "gas", this word is used to name and descriptively track the gas which is produced via a hyperpolarizer to obtain a polarized "gas" product. Thus, as used herein, the term "gas" has been used in certain places to descriptively indicate a hyperpolarized noble gas product and may be used with modifiers such as solid, frozen, dissolved, and liquid to describe the state or phase of that product. Also, for preferred embodiments, the hyperpolarized gas is processed such that it is non-toxic and suitable for delivery to a human subject.

Various techniques have been employed to accumulate and capture polarized gases. For example, U.S. Pat. No. 5,642,625 to Cates et al., describes a high volume hyperpolarizer for spin polarized noble gas and U.S. Pat. No. 5,809,801 to Cates et al. describes a cryogenic accumulator for spin-polarized $^{129}$Xe. Co-pending U.S. application Ser. No. 08/989,604 to Driehuys et al., entitled "Methods of Collecting, Thawing, and Extending the Useful Life of Polarized Gases and Associated Apparatus", describes an improved accumulator and collection and thaw methods. The disclosures of these documents are hereby incorporated by reference as if recited in full herein.

As used herein, the terms "hyperpolarize", "polarize", and the like, mean to artificially enhance the polarization of certain noble gas nuclei over the natural or equilibrium levels. Such an increase is desirable because it allows stronger imaging signals corresponding to better MRI (and spectroscopy) images of the substance and a targeted area of the body. As is known by those of skill in the art, hyperpolarization can be induced by spin-exchange with an optically pumped alkali-metal vapor or alternatively by metastability exchange. See Albert et al., U.S. Pat. No. 5,545,396.

Figure 1:
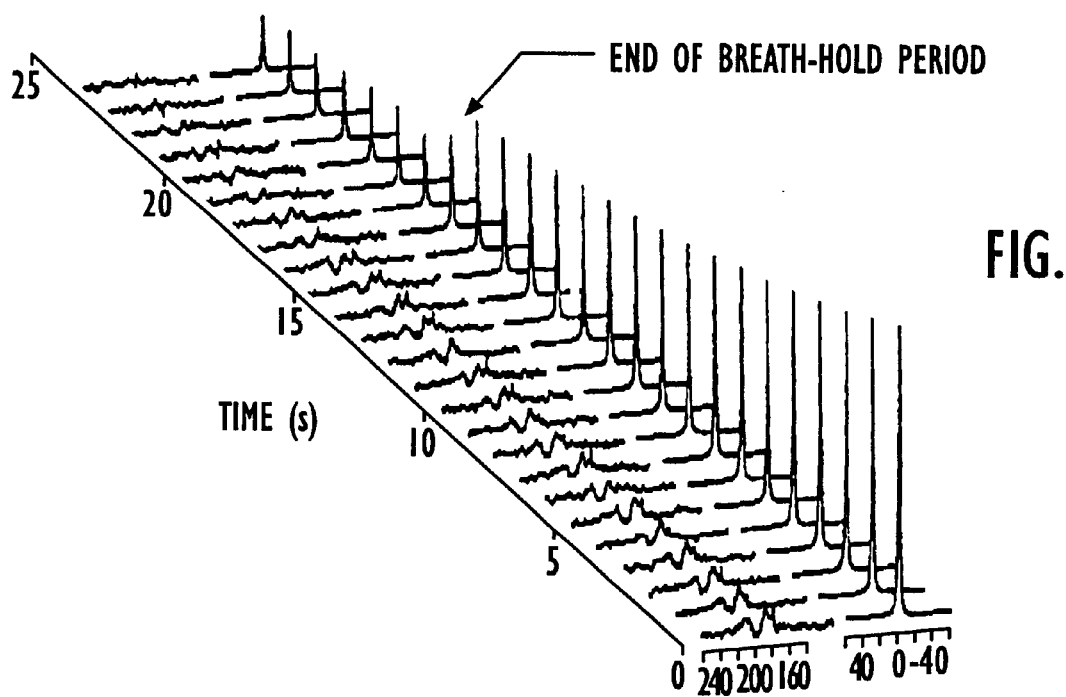
FIG. 1 is a graph of 25 $^{129}$Xe spectra (one spectrum per second) from the chest of a healthy human volunteer, showing the temporal evolution of the gas-phase and dissolved phase signal components during and after a 16-second breath-hold period.

Referring now to the drawings, FIG. 1 illustrates the temporal evolution of the gas-phase and dissolved-phase signal components during and after a 16 second patient breath holding period as shown in Mugler III, et al., supra. The data acquisition began immediately after gas inhalation. The dissolved-phase spectra are shown on the left side of the figure. The vertical scale for the dissolved-phase spectra has been enlarged by a factor of ten over that of the gas-phase spectra (on the right side of the figure). As shown, peaks at approximately 185, 196, and 216 parts per million ("p.p.m.") can be seen in the dissolved-phase spectra. The dissolved phase is thus shifted about 200 p.p.m. of chemical shift along the readout direction between the gas phase of xenon. These spectra were collected using a 10 degree hard RF pulse (so as to equally excite the gas and the dissolved phase components).

Imaging the Pulmonary Vasculature

The method of the instant invention recognizes that FIG. 1 indicates that the dissolved phase xenon signal strength appears to track very closely with the gas-phase signal strength. Accordingly, the present invention further finds that the close tracking of the signal strengths indicates extremely rapid equilibrium of the $^{129}$Xe concentration in the pulmonary blood with the $^{129}$Xe concentration in the lung. In addition, the instant invention recognizes that there is minimal or no build-up of dissolved $^{129}$Xe concentration over time. Thus, the instant invention incorporates the rapid equilibration and lack of magnetization build-up to provide improved imaging methods to obtain clinically useful dissolved phase $^{129}$Xe images.

Generally stated, in a preferred embodiment, a patient is positioned in an MRI unit and exposed to a magnetic field. The MRI unit typically includes a super-conducting magnet, gradient coils (with associated power supplies), a surface coil (transmit/receive RF coil), and a RF amplifier for generating RF pulses set at predetermined frequencies. For $^{129}$Xe imaging at 1.5T field strength, the MRI unit is set to operate in the gas-phase at about 17.6 MHz. Preferably, the dissolved phase excitation frequency is shifted below the gas phase excitation frequency. More preferably the dissolved phase excitation is shifted to be about 200 ppm lower than the gas phase excitation frequency (corresponding to the chemical shift). Thus, in a preferred embodiment, the dissolved phase $^{129}$Xe RF excitation frequency is about 3.52 kHz lower than the associated gas-phase excitation frequency. In yet another preferred embodiment, the imaging method employs a 17.6 MHz gas phase excitation pulse and an associated dissolved phase excitation pulse of preferably about 17.59648 MHz. Of course, the magnet field strength and excitation frequency can vary as is well known to those of skill in the art.

In any event, the RF pulse(s) is transmitted to the patient to excite the nuclei of the polarized $^{129}$Xe. The surface coil is tuned to a selected frequency range and positioned adjacent the targeted imaging region to transmit the excitation pulses and to detect responses to the pulse sequence generated by the MRI unit. Preferred surface coils for standard chest imaging include a wrap-around coil with conductors positioned on both the front and back of the chest. Examples of acceptable coils known to those of skill in the art include a bird cage configuration, a Helmholtz pair, a surface coil, and a solenoid coil (for permanent magnets).

The patient inhales a (predetermined) quantity of polarized $^{129}$Xe gas into the pulmonary region (i.e., lungs and trachea). Preferably, after inhalation, the patient holds his or her breath for a predetermined time such as 5–20 seconds. This can be described as a "breath-hold" delivery. Examples of suitable "single dose" quantities of polarized gases for breath-hold delivery include 0.5, 0.75, and 1.0 liters of gas.

Preferably, the dose at inhalation contains gas with a polarization level above 5%, and more preferably a polarization level above about 20%.

Figure 2:
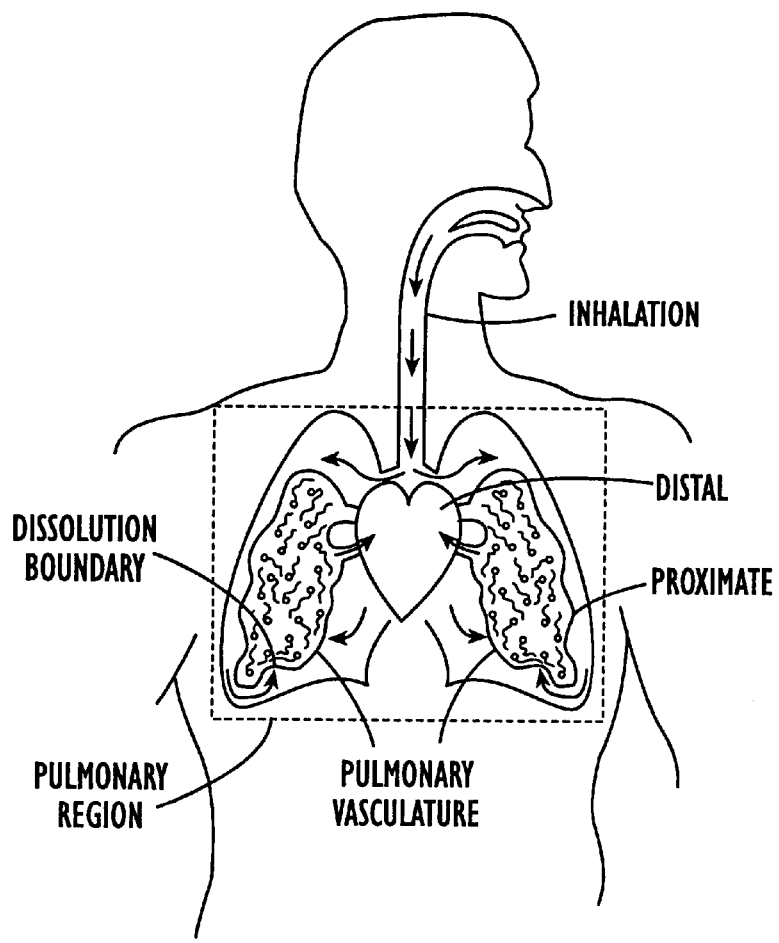
FIG. 2 is a schematic diagram of the human body illustrating dissolution phase imaging according to the method of the present invention.

As schematically shown in FIG. 2, subsequent to inhalation, at least a portion of the polarized gas enters into a dissolved state such that it enters the pulmonary vasculature, including the boundary tissue, cells, membranes, and pulmonary blood vessels such as capillaries, venules, veins, and the like. A substantial amount of the dissolved polarized $^{129}$Xe which enters the pulmonary vasculature then ultimately enters the blood stream with an associated perfusion rate and cycles to the heart via the left atrium, then to the left ventricle and out through the aorta. In the methods according to the instant invention, the dissolved-phase $^{129}$Xe directly enters the venous side of the pulmonary vasculature. However, it is believed that information regarding the arterial side of the vasculature can be obtained due to the symmetry between the venous and arterial passages. For example, it is believed that if there were an arterial blockage, the method of the present invention can generate an "apparent" venous-side defect which corresponds to an "actual" arterial defect.

In overview, according to this preferred method of the instant invention, shortly after inhalation of a suitable amount of hyperpolarized $^{129}$Xe gas (or gas mixture), the MRI unit delivers a large flip angle RF excitation pulse to a selected portion of the pulmonary vasculature. As used herein, large flip angle means an angle which is greater than about 30 degrees. Preferably, the excitation pulse is greater than about 45 degrees. More preferably, the excitation pulse is greater than about 75 degrees and most preferably about a 90 degree excitation pulse. A 30 degree flip angle will generally yield about 50% as much signal as a 90 degree flip (45 degrees typically giving about 70% as much signal).

It is also preferred that the RF excitation is selectively performed. That is, that "selective excitation" is generated such that it excites only certain frequencies, i.e., that it excites substantially only the dissolved phase polarized gas. An exemplary delivery of a selective excitation pulse is via a "hard" pulse. As used herein, "hard" pulse includes pulses where the RF is turned on for a short pulse time ("$t_{pulse}$") and then shortly thereafter, indeed preferably substantially "instantly", turned off. However, short pulse times can yield uncertainty in the associated frequency it generates. Therefore, in a preferred embodiment, selective excitation is performed such that the pulse frequency is centered on the dissolved gas phase resonance desired (i.e., 17.59648 MHz) and has a pulse time, tpulse, such that the associated frequency is below the corresponding gas phase excitation frequency (i.e., 17.6 MHz). For example, one frequency spectrum of a square excitation pulse having a time $t_{pulse}$ and which is centered on a frequency ("fo") can be described by the equation:

$$\sin(a(f-fo)/a(f-fo)),$$

where $a=3.1416*t_{pulse}$.

Therefore, the pulse time $t_{pulse}$ is preferably set so that the sin (a(f–fo))=0 for the gas phase component. Stated differently, the pulse time $t_{pulse}$ is determined according to the relationship $t_{pulse}=1/(f-fo)$. In one embodiment, for a 1.5 T magnetic field strength, f–fo equals 3.52 kHz and $t_{pulse}$ is about 284 $\mu$seconds ($10^{-6}$). Of course, as will be recognized by those of skill in the art, alternative approaches can also be used, such as but not limited to, sine pulses, gaussian pulses, and the like.

In a preferred embodiment, the selective excitation is timed such that it excites the entire pulmonary blood volume. The pulmonary blood volume includes the volume of blood which fills the blood passages associated with the circulatory system between and/or within the lungs and the heart (which can include the volume of blood or a portion of the volume of blood within the boundary lung tissue and/or heart). More preferably, in the method of the present invention, the blood volume of interest is estimated as about half the volume between the right ventricle and the left atrium (because of the expected $T_1$ of the dissolved phase polarized $^{129}$Xe in the blood, it is likely that only the venous side of the circulatory system will include $^{129}$Xe with sufficient polarization levels to provide detectable signal strength). Exemplary volumes will be discussed further below. Advantageously, unlike imaging the gas-phase $^{129}$Xe in the lung where conventionally small flip angles are used to avoid destroying the available magnetization, there is minimal and most likely no penalty for using a large flip angle excitation of the dissolved phase $^{129}$Xe in the pulmonary vasculature because the magnetization will otherwise flow out of the chest region un-imaged. Further, according to the preferred method of the present invention, "fresh" magnetization is substantially continuously flowing in from the capillary beds during the procedure.

The present invention is preferably employed to evaluate blood flow throughout the pulmonary and cardiac vasculature and/or to evaluate blood flow in particular localized regions of the pulmonary and cardiac vasculature. The term "pulmonary and cardiac vasculature" as used herein includes all of the blood vessels within the lungs and/or heart, the chambers of the heart, the passages between the chambers of the heart, as well as the blood vessels between the lungs and heart, and blood vessels between the lungs or heart and other tissues and/or organs. The pulmonary and cardiac vasculature includes, but is not limited to, the pulmonary veins and arteries and associated capillaries, the left and right atria of the heart, the left and right ventricles of the heart, the myocardium, the aorta and aortic arch, the coronary artery, the coronary arteries, the subclavian arteries, and the carotid arteries.

More preferably, the imaging methods of the present invention are carried out to provide clinically useful images of the left and right pulmonary veins and associated capillaries, the left atrium and left ventricle, the myocardium, the ascending aorta, the coronary arteries, the aortic arch, the descending aorta, the left and right subclavian arteries, and the left and right carotid arteries.

Immediately upon inhalation of hyperpolarized $^{129}$Xe into the lungs, Xe begins to dissolve into the pulmonary blood stream. The concentration of Xe in the pulmonary capillary beds ("$[Xe]_P$"), can be assumed to equilibrate instantaneously with the concentration of Xe in the lung gas spaces ("$[Xe]_L$"), thus the relationship can be stated as:

$$[Xe]_P=\lambda[Xe]_L, \tag{1}$$

where "$\lambda$" is the Xe blood/gas partition coefficient or blood solubility. This concentration can be expected to equilibrate in the venous side of the pulmonary vasculature just a few seconds after inhalation as will be discussed further below. The standard unit for concentration is an "amagat" which refers to 1 atmosphere of gas pressure at a temperature of 273 K. For humans whose lungs contain one atmosphere of gas and whose temperature is about 310 K, all gas densities should be scaled down by a factor of about A=0.88 amagat per atmosphere. For a patient inhaling a volume ("$V_{Xe}$") of Xe into their lungs of volume ("$V_L$"), the resulting Xe density in the lung $[Xe]_L$ will be $$[Xe]_L = A \frac{V_{Xe}}{V_L}. \qquad (2)$$

Thus, the concentration of Xe in the pulmonary blood $[Xe]_P$ will be related to the inhaled gas volume $V_{Xe}$, and can be stated by the expression:

$$[Xe]_P = \lambda A \frac{V_{Xe}}{V_L}. \qquad (3)$$

For reference, an estimate of $\lambda$ for Xe in blood is that $\lambda \approx 0.15$. Thus, as an example, a patient who inhales 1 L of Xe into his 6 L lung will yield a Xe density in the lungs of $[Xe]_L \approx 0.15$ amagat, and correspondingly a Xe density in the pulmonary capillary beds of $[Xe]_p \approx 0.02$ amagat. Thus, the dissolved polarized $^{129}$Xe gas in the pulmonary capillary beds is approximately ⅙ the concentration of the lung gas.

In operation, upon crossing the gas/blood barrier, the dissolved polarized $^{129}$Xe is transported out of the lung into the heart and then out to the remainder of the body. However, as noted above and generally stated, once the $^{129}$Xe has been transported out of the heart, it is likely that it will no longer be useful for pulmonary or cardiac imaging. Therefore, it is preferred that the imaging is performed in a manner which uses the polarization before it is transported out of the heart and dispersed into the body, potentially resulting in a loss of the useful pulmonary (and/or cardiac) vasculature magnetization.

The timescale for $^{129}$Xe transport out of the pulmonary region or chest area ("$t_p$") is a function of pulmonary blood flow rate ("Q") and pulmonary blood volume ("$V_p$") which can be expressed by the following:

$$t_p = \frac{V_p}{Q}. \qquad (4)$$

Thus, to determine $t_p$, one can assume that the volume of pulmonary venous blood between the lung and the heart ("$V_p$") is such that $V_p \approx 200$ cubic centimeters ("cc") and that the pulmonary blood flow rate (Q) is approximately Q≈80 cc/s. See R. M. Berne, *Physiology* (Mosby-Yearbook, Inc., St. Louis, Mo., 3d ed. 1993). With these numerical assumptions, the transit time from lung to heart is determined to be less than 3.0 seconds, and more particularly $t_p \approx 2.5$ seconds. Of course, as will be understood by those of skill in the art, alternative blood volumes will yield alternative transit times. For example, another conventional source estimates a blood flow of about 5.5 L/min (92 cc/sec) and a total blood volume in the pulmonary vessels at any one time of about 1.0 L (of which 100 ml are in the capillaries). According to one method of the instant invention, the relevant blood volume would be 500 ccs from the lung to the heart and the time from dissolution to entry into the heart is then about 5 seconds. Correspondingly, the transit time out of the capillaries is then about 0.5 seconds. Thus, the image sequence will depend on the imaging region or volume of interest. Further, as will be appreciated by those of skill in the art, children and smaller adults can have less volume while larger adults can have more, and the corresponding image times can vary accordingly.

In a preferred imaging method of the instant invention, the delay between the large angle (preferably 90 degree) RF excitation pulses is preferably less than $t_p$. As will be discussed below, it may be advantageous to further shorten this delay time. In any event, for $T_R$ less than or equal to the time $t_p$, signal strength in the (perfusion) image will be substantially linearly proportional to the inhaled gas volume and the $^{129}$Xe polarization level of the inhaled gas.

Accordingly, care should be taken when setting the excitation pulse repetition interval $T_R$. This is because the setting of $T_R$ will affect both image SNR and determine, to some extent, which parts of the lung or cardiac vasculature will be visualized. A long $T_R$ will result in $^{129}$Xe polarization or magnetization that is (uniformly) distributed throughout the veinous side of the pulmonary vasculature. A very short $T_R$ setting results in imaging Xe substantially in the capillary beds of the lungs. This is because the large flip angle pulse substantially destroys the incoming $^{129}$Xe polarization or magnetization before it reaches the larger vessels and thus the larger blood vessels would not be rendered visible. Therefore, if it is desired to emphasize or detect emboli in the smaller capillaries, one can restrict imaging to the smaller vessels by using short repetition times, and even if the small vessels cannot be resolved individually, a perfusion-associated defect should nonetheless be detectable.

Figure 3:
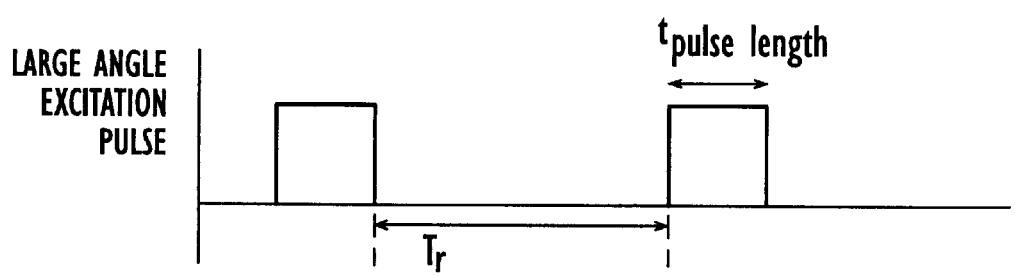
FIG. 3 is a graphical representation of a large angle radio frequency ("RF") excitation pulse sequence and exemplary corresponding echo sequences according to one of the methods of the present invention.

As shown in FIG. 3, the excitation pulse repetition time ($T_R$) is associated with either a single echo or multi-echo pulse acquisition sequence. For each RF pulse, a multi-echo data acquisition is preferably performed such that there are at least four received echoes between each excitation pulse. Preferably, for a breath-hold delivery of 10 seconds, four RF dissolved phase excitation pulses (about 2.5 seconds apart) are generated. Further preferably, for each RF pulse, at least 32 corresponding echoes are generated. Further, because increasing numbers of echoes will allow increased amounts of signal to be extracted from the dissolved gas. Thus, for example, for a 10 second breath-hold delivery and a $T_R$ of 2.5 seconds, for 128 echoes collected for each RF excitation, the SNR can be improved by a factor of 2 over the 32 echo pulse embodiment described above.

The repetition time $T_R$ of FIG. 3 is preferably 0.01–3.0 seconds. In one embodiment, for single echoes, the repetition time between excitation pulses is set at 78 ms or less as will be discussed further below. More preferably, the repetition time is set such that it corresponds to the time it takes for a given volume of blood to move from the lungs to the heart ("$t_p$"), estimated as stated above at under 3.0 seconds and preferably at about 2.5 seconds. Further, the repetition time can be adjusted to image specific portions of the pulmonary region. For example, the repetition time can be decreased to emphasize a signal from capillaries in the pulmonary region. In contrast, the repetition time can be increased to emphasize vasculature which is a further distance from the pulmonary region.

Unlike imaging the gas-phase of the polarized $^{129}$Xe in the lung, where conventionally small flip angles are used to avoid destroying the available magnetization, there is minimal or no penalty for using a large flip angle excitation of the dissolved phase polarized $^{129}$Xe because it will otherwise flow out of the chest region un-imaged. Indeed, a rapid 90 degree pulse imaging sequence makes optimal use of the dissolved $^{129}$Xe polarization or magnetization. The excitation repetition rate should be fast enough to capture the $^{129}$Xe before it flows out of the chest region. Such an imaging method can provide two (2) and three (3) dimensional dissolved phase images of the pulmonary vasculature.

In a preferred embodiment, an entire perfusion image (MR image directed to the dissolved phase polarized gas) is generated in a single breath-hold period ("$T_B$"). For example, one can use a slice-selective image in which the chest is divided into a number of slices ("$N_s$"). A typical MR image slice comprises a number of phase encode steps ("$N_{pe}$") and a number of frequency encode steps ("$N_{fe}$"). Typical numbers of these steps are $N_{pe}$=128 and $N_{fe}$=128 (or 256). For single echoes derived from each excitation, 128 separate RF excitations can be used to generate a single image. Single echoes may be preferred where there are relatively short $T_2^*$ periods (dissolved phase transverse relaxation times) or adverse blood flow effects.

The number of RF pulses ("$N_{rf}$") which can be generated in a single breath-hold time is related to repetition time ($T_R$) and breath-hold time ($T_B$), and can be expressed by:

$$N_{rf} = \frac{T_B}{T_R}. \tag{5}$$

Accordingly, for illustrative purposes, for single-echo imaging with a breath-hold period $T_B$=10 s, then the repetition time is preferably set such that $T_R \leq 78$ ms for a single image slice.

In view of the foregoing, the signal strength expected in a given image voxel can be analyzed as a function of the image parameters. The effective pulmonary volume imaged ("$V_{eff}$") can be determined by blood flow rate (Q) and pulse repetition time ($T_R$), expressed by the following:

$$V_{eff} = T_R Q. \tag{6}$$

To calculate the polarization or magnetization in a given pulmonary voxel ("$V_{iP}$") one can divide the effective pulmonary image volume ($V_{eff}$) by the image matrix size, as expressed by equation (7).

$$V_{iP} = \frac{T_R Q}{N_s N_{pe} N_{fe}} \tag{7}$$

The total signal in each pulmonary vasculature voxel ("$S_{iP}$") is proportional to the product of coil gain ("G"), $^{129}$Xe polarization ("$P_{Xe}$"), the concentration or density of $^{129}$Xe in the vasculature ([Xe]$_P$), voxel volume ("$V_{iP}$"), and the sine of the excitation angle used in the pulmonary vasculature ("sin $\alpha_P$"). Thus, the relationship can be expressed as follows:

$$S_{iP} = \frac{G P_{Xe} \lambda [Xe]_L T_R Q \sin \alpha_P}{N_s N_{pe} N_{fe}}. \tag{8}$$

Similarly, the signal strength per voxel of $^{129}$Xe in the lung ("$S_{iL}$") can be stated by equation (9) (the expression "sin $\alpha_L$" representing the excitation angle used in the lung).

$$S_{iL} = \frac{G P_{Xe} [Xe]_L V_L \sin \alpha_L}{N_s N_{pe} N_{fe}} \tag{9}$$

Comparing the signal strength in equations (8) and (9) gives a ratio of signal strengths per voxel of dissolved versus gaseous polarized $^{129}$Xe as stated in equation (10).

$$\frac{S_{iP}}{S_{iL}} = \frac{\lambda T_R Q \sin \alpha_P}{V_L \sin \alpha_L}. \tag{10}$$

As an example, for 128 phase encoding steps, the gas phase image can be made with $\alpha_L$=7° and the perfusion image with $\alpha_P$=90°. Thus, in this example, for $T_R$=78 ms, as calculated above for single-echo imaging, then the relative signal strengths can be estimated as follows:

$$\frac{S_{iP}}{S_{iL}} = \frac{.15 \times .078s \times 80 \text{ cm}^3 s^{-1}}{6000 \text{ cm}^3 \times 0.12} \approx 1 \times 10^{-3}. \tag{11}$$

While the signal strength per voxel is dramatically lower in the dissolved phase than in the gas phase, this lower signal strength does not prevent clinically useful perfusion imaging according to the instant invention as described herein.

Additionally, steps can be taken to increase the signal per voxel for the perfusion imaging of the pulmonary vasculature as described above. First, one may choose to decrease image resolution to increase signal strength. In one embodiment, for example, one may choose not to perform slice-selective imaging. A full projection image of the chest reduces the number of image slices ("$N_s$") to $N_s$=1 from $N_s$=16 for slice-selective imaging with 1 cm thick slices. Further, the frequency-encode steps ($N_{fe}$) combined with the non-slice selective imaging yields a factor of 32 SNR increase per voxel in the perfusion image.

A reduction in the number of phase encode steps has two beneficial effects on image SNR. First, a reduction by 2 of $N_{pe}$ gives a factor of 2 increase in voxel SNR akin to reducing $N_{fe}$. Furthermore, in the single-echo imaging discussed so far, a reduction in $N_p$ implies a corresponding reduction in the number of RF excitations required $N_{rf}$. This allows us to increase the repetition time $T_R$, which allows more time for magnetization to flow from the lung into the pulmonary vasculature. Accordingly, reducing $N_{pe}$ by 2 provides another factor of 4 in SNR per voxel, bringing the total signal gain per voxel to 128. Thus, with some resolution sacrifice, signal strengths per voxel of $^{129}$Xe in the pulmonary vasculature can be about 8%–10% or more of the corresponding voxel signal strength in the lung (i.e., $S_{iP} \approx 0.1 S_{iL}$).

The image matrix of Mugler III et al. was 64×128×11 for a gas phase image of the lung. The voxel SNR was 32 for this image. Given this data and the steps suggested above, a dissolved phase image of the pulmonary vasculature, using single-echo 90° excitations spaced 78 ms apart can be made with a matrix size of 64×64×1 with an SNR of 1.6 in each voxel. Further, as described in co-pending application to Driehuys et al., "Methods of Collecting, Thawing, and Extending the Useful Life of Polarized Gases and Associated Apparatus", (incorporated by reference hereinabove), reliable $^{129}$Xe polarizations of well above 10% are now achievable. This is in comparison to the 2% polarization level described in the Mugler III et al. disclosure. In addition, various surface coil improvements such as tuning, configuring the coil to have close physical alignment with the body volume of interest, new coil technology known to those of skill in the art as circular polarization ("CP"), and the like, can yield another factor of 2√2 improvement. Thus, and advantageously, this permits an increase in SNR (an improvement of about 30 is possible), indicating that a pulmonary image of the stated matrix size (64×64×1) can be made with a voxel SNR of about 45.

Signal to noise ratio ("SNR") improvements in the images can be obtained by using one or more of thick slices (no slice select), reduced image matrix size, multi-echo imaging, and signal averaging. In addition, when multiple echoes ($N_e$) are used, the number of RF excitation pulses can be decreased. Further, alternative imaging strategies can be used. For example, for multiple echoes (1) $T_R$ can be kept constant and more images can be generated (multi-slice, dynamic imaging, etc.) (2) $T_R$ can be lengthened and thus more area of the vasculature can be imaged, and (3) $T_R$ can be kept constant and the multiple echoes can be used to average lines in k-space to increase the image SNR. For example, if four echoes are made from each excitation, the same line in k-space can be imaged four times on each excitation and thereby advantageously increase the image SNR by 2.

As noted above, further signal gains can be obtained if multi-echo imaging strategies are successfully implemented. Therefore, and preferably, the MRI unit generates subsequent multi-echo image acquisition, although a single echo imaging is also possible as described above. For $^{129}$Xe dissolved in blood, it is expected that the transverse relaxation time ("$T_2$*") is relatively long (on the order of 100 ms or more). In the absence of undesirable flow effects, one can generate multiple echoes within this time. Each echo generated is preferably a phase-encode step. As an estimate, one can make as many as 30 echoes in 100 ms. This number of echoes can allow a large reduction in the number of RF excitations ($N_{rf}$) and thus further lengthen the repetition time ($T_R$), and increase the SNR per voxel. Preferably, the upper limit for the repetition time of $T_R$ is to set it equal to the blood transit time out of the lung $t_p$. For $T_R=T_p=2.5$ s is set as discussed above, then four RF excitations can be generated during a 10 second breath-hold period. In order to generate 128 phase encode steps, 32 echoes per excitation are used. Therefore, for 32 echoes, the SNR per voxel is increased by a factor of 32 (2500/78=32) over the single echo imaging technique described above. That is, the signal gain is linear with echo number, and preferred imaging methods of the instant invention include multi-echo imaging. With such a signal increase, the previous estimate suggests that the image matrix size can be increased to 128×256×10 with a voxel SNR of 8. Thus, multi-echo imaging can allow slice-selective imaging as well.

Preferably, when multi-slice imaging is employed, the slice acquisition is performed by interleaving the slices. A slice-selective acquisition will only excite spins in a given slice of the lung. Once a slice has been excited (and a line of k-space) has been obtained, that slice is not excited again until the time $T_R$ has elapsed and spins (in the magnetized polarized dissolved gas) have flowed back into the slice. However, alternate slices can be excited and imaged during this "waiting" period. Advantageously, such interleaving of slices allows image acquisition time to be minimized.

One concern for multi-echo imaging methods is the flow of blood and the affect on the ability to (re)focus the echoes. Thus, multi-echo imaging methods may be facilitated by the use of cardiac-gated imaging, and to do all imaging during diastole, the period when blood flow is slowest. In one embodiment, cardiac gating is used to better time/sequence image acquisition to correspond with the period of slow blood flow in the patient. Alternatively, other methods of slowing the blood circulation such as delivering sedatives or anesthesia to the patient to slow the heart rate may be employed to facilitate multi-echo image acquisition.

As will be appreciated by those of skill in the art, imaging with polarized dissolved gas depends on transport of sufficient surviving polarization or magnetization to tissues of interest. In a preferred embodiment, the tissues of interest include the pulmonary region, and particularly the pulmonary vasculature. As will also be appreciated by those of skill in the art, polarization decays corresponding to the longitudinal relaxation time, T1. Dissolved phase $^{129}$Xe can have a relatively short relaxation time (T1) generally thought to be due to the presence of oxygen and due to paramagnetic deoxyhemoglobin in the blood. For example, T1 for substantially fully oxygenated human cell membranes is estimated at about 15 seconds. Alternatively, T1 in blood has also been estimated as about 5 seconds. See A. Bifone et al., 93 Proc. Natl. Acad. Sci., p. 12932 (1996). Taking the estimated upper limit of about a five second transit time to the heart as discussed above, the xenon polarization can be attenuated to about ⅓ of its starting value at the heart. This relationship supports that $T_R$ should be shortened to less than about 2.5 seconds, and preferably less than about 1–2 seconds. Correspondingly, with about a 2.5 second transit time, the magnetization can be calculated as noted above to be about 0.61 of its starting magnetization.

As is also known to those of skill in the art, the polarized $^{129}$Xe also has an associated transverse relaxation time, $T_2$. In the dissolved phase, as noted above, it is estimated that this $T_2$* is relatively long. Taking advantage of this characteristic, it is preferred that (especially for $T_2$*'s which are greater than about 100 ms), multi-echo acquisition methods are used. As will be appreciated by those of skill in the art, examples of suitable multi-echo methods include Echo Planar Imaging ("EPI"), Rapid Acquisition with Relaxation Enhancement ("RARE"), FSE ("Fast Spin Echo"), Gradient Recalled Echoes ("GRE"), and BEST. Examples of some suitable pulse sequences can be found in an article by John P. Mugler, III, entitled *Gradient-Echo MR Imaging*, RSNA Categorical Course in Physics: The Basic Physics of MR Imaging, 1997; 71–88. For example, the article illustrates an example of a standard single RF spin-echo pulse sequence with a 90 degree excitation pulse and a 180 degree refocusing pulse. In this diagram, $G_P$ is a Phase-encoded gradient, $G_R$ is the readout gradient, $G_S$ is the section-select gradient, and RF is the radio frequency. The article also illustrates a Gradient Recalled Echo pulse sequence (GRE) with a flip angle α and a Rapid Acquisition with Relaxation Enhancement (RARE) pulse sequence as well as a single shot Echo Planar Imaging (EPI) pulse sequence with gradient recalled echoes.

In summary, according to a preferred embodiment of the pulmonary vasculature imaging method of the present invention, a single breath inhalation volume "Vxe" of about 0.5–1.25 liters of polarized $^{129}$Xe is delivered to a patient for a breath-hold time $T_B$ of about 5–15 seconds. Longer breath-hold times will allow an increased dissolved-phase polarized gas perfusion signal to be extracted from the polarization or magnetization delivered via the lung. In this embodiment, the large flip angle excitation pulse ("$α_P$") is about 90°. Preferably, the excitation pulse is tailored in frequency and duration to affect only the dissolved $^{129}$Xe ("selective excitation"), leaving the gas-phase magnetization in the lung substantially undisturbed.

Thus, during the breath-hold period, the hyperpolarized $^{129}$Xe in the lung decays corresponding to the longitudinal relaxation time T1 and the uptake (e.g., absorption, diffusion, or dissolution) of polarized $^{129}$Xe into the blood. From generally known oxygen related effects, the gas phase T1 for polarized $^{129}$Xe in the lungs is estimated at about 35 seconds. The decay time constant of magnetization in the lung due to blood uptake is generally described by the equation $T_Q=V_L/(λ.Q)$. This equates to about 500 seconds and therefore presents a negligible polarization or magnetization decay of the lung gas over the breath-hold period. The effective T1 is reduced to about 33 seconds when this effect is included. For $T_B=10$ seconds, the $^{129}$Xe magnetization in the lung (and the associated dissolved or perfused $^{129}$Xe magnetization or polarization) will be reduced according to the equation ($e^{-10/33}=0.74$) of the starting magnetization value.

In a preferred embodiment, the pulse repetition time $T_R$ is selected for optimal image contrast where $T_R$ is less than or equal to $t_p$ (the time it takes for the blood with the dissolved polarized $^{129}$Xe to travel from the lungs to the heart). As noted above, a shortened $T_R$ emphasizes signal from capillary beds while a longer $T_R$ can show substantially all of the pulmonary vasculature.

As noted above, the dissolved phase imaging can be used to advantageously detect a pulmonary embolus. As will be appreciated by one of skill in the art, emboli tend to occur in the arterial side of the pulmonary vasculature, while the $^{129}$Xe uptake tends to occur on the venous side of the pulmonary vasculature. However, it is believed that symmetry in the venous-arterial branching will allow arterial defects to appear on the venous side. For example, for a patient with a blood clot or obstruction in the left pulmonary artery which occludes substantially all blood flow, then the $^{129}$Xe dissolved phase image will show minimal or no left lung vasculature in the image because there is no flow to carry the polarized xenon from the capillary beds forward. Similarly, if the obstruction or clot is in the first branch of the left pulmonary artery, the corresponding dissolved phase ("perfusion") image will not show a portion of the venous vasculature before the first branching on the venous side. Further, when imaging to detect emboli, sufficient resolution techniques should be employed to help assure that any embolus in a given arterial vessel is detected. Thus, image resolution should be such that it corresponds to typical embolism size, vasculature location and vasculature structure (venous branching).

In a preferred embodiment, due to the approximately 200 p.p.m. chemical shift between the gas and dissolved phase resonance of the polarized $^{129}$Xe, at least two images including both a perfusion and ventilation image is generated on a patient during the same imaging session ("differential" imaging). Advantageously, differential images provide additional image information. For example, the differential image can help distinguish between a pulmonary embolus and a matched ventilation/perfusion defect associated with a structural anomaly. In one embodiment, the inhalation image is generated using polarized $^3$He while the perfusion image uses polarized $^{129}$Xe. Preferably, the images are generated from two data sets captured on two separate imaging sequences. For images using $^{129}$Xe as both the inhalation and perfusion medium, the same breath-hold delivery cycle can be employed for both sets of image data. In such an embodiment, it is preferred that the perfusion image is generated during the first 10 seconds of the breath-hold cycle and the remaining gas in the lung is used for a ventilation image, i.e., the last five seconds of the delivery cycle. Of course, separate breath-hold delivery cycles can also be used. In any event, differential imaging will allow better images with information which correlates the total region (lung space and boundary regions). This should also produce images which detect emboli, perfusion defects, and other circulatory system problems in the pulmonary and/or cardiac vasculature.

Cardiac Imaging Method

Similar to the pulmonary vasculature imaging method described above, the instant invention also includes cardiac imaging methods using dissolved hyperpolarized $^{129}$Xe to image the heart and cardiac blood vessels (in particular, major cardiac blood vessels). As described above, after inhalation, the dissolved phase $^{129}$Xe is transported in the blood flow path of the pulmonary vasculature to the heart. Subsequent to inhalation, at least a portion of the polarized gas enters into a dissolved state which enters the pulmonary vasculature, including the boundary tissue, cells, membranes, and pulmonary blood vessels such as capillaries, venules, veins, and the like. More specifically, a substantial amount of the dissolved polarized $^{129}$Xe ultimately enters the blood stream with an associated perfusion rate and cycles to the heart via the left atrium, then to the left ventricle and out of the heart. Generally stated, as will be appreciated by those of skill in the art, there is limited or no vascular branching in the blood flow path of the heart until after the left ventricle. As such, imaging the left side of the heart (atrium and ventricle) can be performed with the dissolved phase polarized $^{129}$Xe in the associated blood flow path similar to the methods described for imaging the pulmonary vasculature discussed above. Like the pulmonary imaging method, it is preferred that large angle excitation pulses are generated in a MRI system and that those pulses are timed in accordance with the blood replenishment rate to the region of interest.

The inhaled polarized $^{129}$Xe in the lung gas space acts as a substantially continuous supply of polarized $^{129}$Xe for dissolution and entry into the pulmonary blood. Preferably, the large angle pulse "selectively" excites only the blood-dissolved $^{129}$Xe, leaving the lung with a sufficient quantity of polarized gas at a sufficient polarization level (i.e., magnetized) and thus available for a substantially continuous supply for the gas to migrate to and enter a dissolved phase in the pulmonary vasculature, and ultimately the associated blood stream during the imaging procedure. As before, the timing of the RF pulses are dependent on the volume of the region to be imaged ("V") and the blood flow rate (Q) as expressed by equation (4). The volume of the left ventricle (V) varies between about 140 ml and 60 ml depending on the phase of the cardiac cycle. The blood flow rate (Q) is estimated as above (at about 80 cc/s), while $T_p$ for the left ventricle is estimated to be above 0.5 and below 2 seconds. More particularly, using the above stated parameters, $T_p$ is estimated as between about 0.8–1.8 seconds; $0.8 \text{ s} \leq t_p \leq 1.8 \text{ s}$. Accordingly, it is preferred that the RF pulse repetition interval $T_R$ be set such that it is less than or equal to the corresponding blood flow time $t_p$. Of course, any initial pulse should be timed to allow the dissolved $^{129}$Xe to be transported to the heart (i.e., 2.5–3.5 seconds after inhalation). Subsequent pulses are preferably timed to obtain signals from the dissolved polarized gas while minimizing the destruction of incoming magnetization. This will allow additional excitation pulses without waiting for the entire vasculature to be refilled with unaffected dissolved polarized gas.

Figure 4:
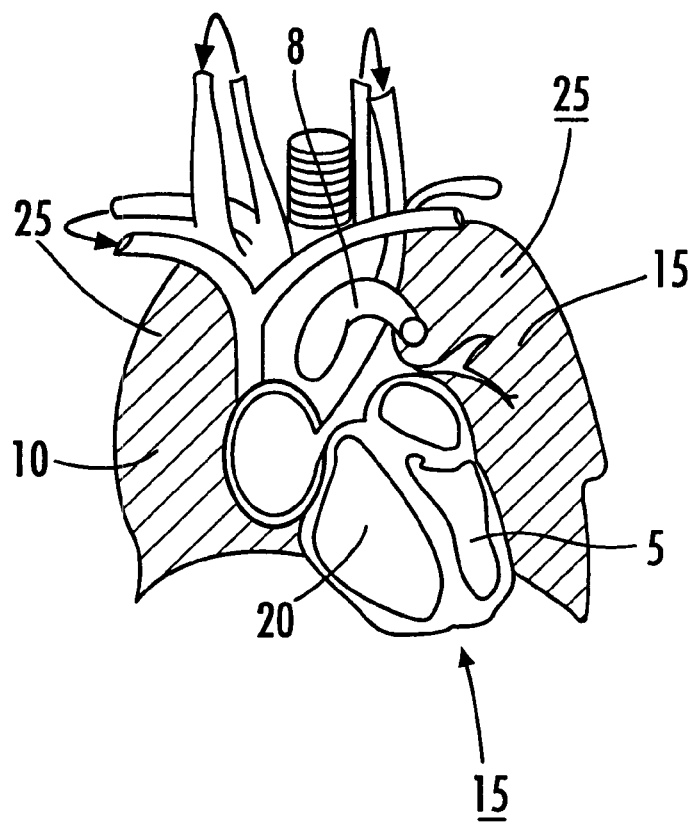
FIG. 4 is a schematic diagram of the human blood vascular system showing the dissolved $^{129}$Xe blood flow path according to one embodiment of a method according to the present invention.
Figure 5:
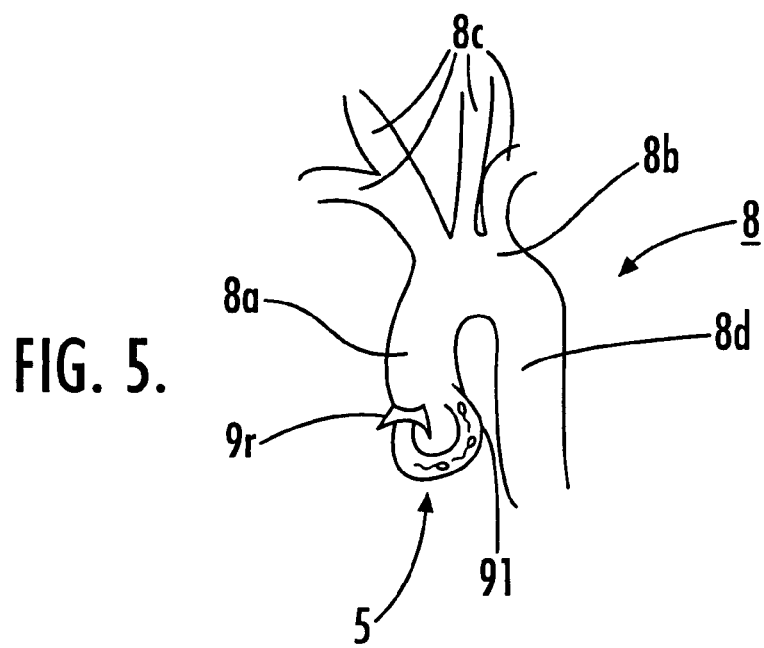
FIG. 5 is a schematic diagram of the aorta shown of FIG. 4.

The cardiac imaging method also can be beneficially used to image the heart beyond the left ventricle 5. FIG. 4 shows a section view of the heart 15 with the lungs 25. As shown, the heart 15 includes left and right ventricles 5, 20 and the aorta 8. As also shown, the lungs 25 include right and left lungs 10, 15. As illustrated by FIGS. 4 and 5, blood flows from the left ventricle 5 up the ascending aorta 8*a* where the first branching is to the coronary arteries 9*r*, 9*l*. Perfusion imaging (dissolved phase polarized $^{129}$Xe imaging) of these coronary arteries 9*r*, 9*l* can provide valuable information about the condition and status of these arteries, such as blockage, thickening, and the like. As shown in FIG. 5, continuing along the blood flow path after the coronary arteries 9*r*, 9*l*, is the aortic arch 8*b*, a quadruple branching at the top of the arch 8*c* (to the right and left carotid arteries and the right and left subclavian arteries) and then the descending aorta 8*d*. As the dissolved $^{129}$Xe flows along this blood flow path, the signal is sufficiently strong as to render clinically useful images. In summary, the imaging methods of the present invention can render clinically useful images of target regions which include, but are not limited to, the left and right pulmonary veins and associated capillaries, the left atrium and left ventricle, the myocardium, the ascending aorta, the coronary arteries, the aortic arch, the descending aorta, the left and right subclavian arteries, and the left and right carotid arteries. Of course, using polarized gas with increased polarization levels (i.e., above 20%) can further expand the dissolved phase imaging regions.

Further, it is anticipated that perfusion images according to the methods of the instant invention can be used in regions or organs which absorb or pass blood such as, the brain, the liver, and the kidney. In this application, one can use the methods as described herein, recognizing that some of the polarized dissolved-phase $^{129}$Xe will be retained in the respective tissues at different chemical shifts. However, as described above, volume calculations of the region or area of interest can be used to determine the pulse repetition rate to maximize the use of the dissolved polarization-related signal.

In a preferred embodiment, the method of the present invention uses a small close-fitting cardiac surface coil to deliver the excitation pulse rather than a conventional body coil. This will allow improved SNR and spatially limit the RF pulse to this smaller region, thereby minimizing the incidental destruction of the $^{129}$Xe incoming from the pulmonary vasculature.

In an additional preferred embodiment, the method of the present invention uses a pulse and gradient combination which is selective. This selection can be slice or volume selective. Conventional imaging methods are generally "slice" selective. Slice selective images are typically generated by combining a frequency-selective pulse in the presence of a z field gradient ("$G_z$"), excitation can be confined to a slice of thickness "$\Delta z$" along the z axis. The z field is defined as the axis which extends along the length of the body. The frequency bandwidth of the excitation pulse together with the gradient, confines excitation to the nuclei in the slice, substantially no signals are excited or detected from areas outside the defined slice.

Volume-selective imaging allow a two-dimensional spatial localization using a single pulse. These methods employ RF pulse/gradient combinations which excite a filled cylinder of spins. In a preferred embodiment, a volume-selective pulse is used, and more preferably, a cylindrical imaging volume selection is used. It is believed that the volume selection is particularly suitable for cardiac perfusion images because they can advantageously allow coronary artery images while also minimizing background signal from the left side of the heart. See C. J. Hardy and H. E. Cline, *Broadband nuclear magnetic resonance pulses with two-dimensional spatial selectivity*, J. Appl. Phys., 66(4), Aug. 15, 1989; C. J. Hardy et al., *Correcting for Nonuniform k-Space Sampling in Two Dimensional NMR Selective Excitation*, 87 Jnl. Magnetic Resonance, 639–645 (1990); and *Spatial Localization in Two Dimensions Using NMR Designer Pulses*, Jnl. of Magnetic Resonance, 647–654 (1989).

A pulse-gradient combination can also limit the collateral damage to the incoming magnetization, thereby maximizing the image SNR. It is also preferred that multiple echo signals be used (i.e., multiple gradient-recalled or RF-recalled echoes) to increase image SNR (linearly) with the number of echoes as discussed under the pulmonary imaging method.

An additional alternative to cardiac imaging is to directly deliver polarized $^{129}$Xe to a region of the heart (such as via injection and the like into the left ventricle muscle) to image the perfusion of the heart. Delivery directly to the right atrium/ventricle can allow perfusion imaging of the return side of the heart. In any event, the polarized $^{129}$Xe delivery can be via injection of various phases/vehicles such as but not limited to gaseous, dissolved, or liquid phase. Conventional image perfusion methods for this area employ radioactive tracers such as Thalium ("$^{201}$Tl") or Technetium ("$^{99m}$Tc"). Using xenon, which is an inert noble gas, can beneficially replace radioactive tracers which can expose the subject to potentially dangerous elements.

Methods to Evaluate Blood Flow

In addition to the imaging methods described above, the instant invention also includes MR spectroscopic methods which can be used to evaluate the lung and heart blood flow by using the dissolved-gas phase of the $^{129}$Xe inhaled gas which enters the vasculature (lung perfusion) and the blood stream as described above. Generally described, the instant method is relatively inexpensive and advantageously employs the inhaled hyperpolarized $^{129}$Xe (as discussed above) to evaluate blood flow in a low-field NMR spectroscopy system. The terms "evaluate" and "evaluating" as used herein are intended to be interpreted broadly and mean that the blood flow of a subject is measured, determined, quantified, observed, monitored, imaged, and/or assessed.

The term "blood flow" as used herein is to be broadly construed. Methods of evaluating blood flow according to the present invention encompass methods of determining blood flow rates, perfusion (typically measured in ml/min/g tissue), comparative blood flow values (monitoring blood volume or flow rates as changes over time such as before and after drug therapy or surgical treatment or real time feed back during surgery to verify success of treatment—without the need for absolute values), blood volume, or blood path anomalies, in particular, in the pulmonary and/or cardiac vasculature. Also included in the inventive methods of evaluating blood flow are methods of determining the presence of absence of an obstruction to blood flow or local defects in blood passage through the vasculature (e.g., from stenosis), in particular, the pulmonary and/or cardiac vasculature.

As described above (such as in Equations 1–6), a patient who inhales 1 L of Xe into the lungs (having about a 6 L lung volume) will yield about or dissolve into about ⅙ of that value of the xenon concentration (0.02 amagat) in the pulmonary vasculature and associated blood. In a preferred embodiment, the method uses frequency selective large angle (more preferably 90°) RF excitation pulses which substantially depletes the $^{129}$Xe in the pulmonary blood but leaves the hyperpolarized gas in the lungs substantially undisturbed. In this embodiment, the repetition time interval between RF pulses ($T_R$) and the pulmonary blood flow rate (Q) can be used to determine the effective pulmonary volume ($V_{eff}$) containing (dissolved phase) hyperpolarized $^{129}$Xe. See equation 6, supra. This relationship assumes that $T_R$ is less than or substantially equal to the time it takes for the polarized $^{129}$Xe to leave the pulmonary blood ($t_p$). As discussed above, for typical blood flow rate and estimated volume of venous pulmonary blood, $t_p$ is approximately 2.5 seconds. Thus, with a large RF excitation pulse (preferably, about $\alpha$=90°), the dissolved pulmonary $^{129}$Xe signal strength in the pulmonary blood is proportional to the product of coil gain ("G"), Xe polarization ("$P_{xe}$"), and polarized Xe density or concentration in the vasculature ($[Xe]_P = \lambda[Xe]_L$), which can be stated by the following expression:

$$Sp(T_R) = GP_{xe}\lambda[Xe]_L \, QT_R \quad (12)$$

Notably, the signal strength is dependent on both the pulse interval ($T_R$) and the blood flow rate (Q). The dissolved signal intensity versus repetition time will have an associated slope which can be mathematically expressed as follows:

$$\frac{dS_p}{dT_R} = GP_{Xe}\lambda[Xe]_L Q \quad (13)$$

The slope is directly proportional to the pulmonary blood flow rate (Q). Calibration of the blood flow rate is obtainable by evaluating the gas phase signal ("$S_L$") in the lung, the signal having an associated small RF tipping angle (excitation angle) ("$\alpha_L$"). The gas phase signal can be expressed by the equation:

$$S_L = GP_{Xe}[Xe]_L V_L \sin \alpha_L \quad (14)$$

The pulmonary blood flow rate (Q) can be stated by the ratio of the hyperpolarized $^{129}$Xe gas and dissolved phase signals. This ratio cancels receiver gain (G) and polarization value $P_{xe}$. Accordingly, the blood flow rate (Q) can be expressed by the following:

$$Q = \frac{V_L \sin \alpha_L (dS_p/dT_R)}{\lambda S_L} \quad (15)$$

Advantageously, with measurements of the Xe/blood partition coefficient ($\lambda$) and the total lung volume ($V_L$), a quantitative measurement of blood flow is established according to a method of the instant invention. As will be appreciated by one of skill in the art, lung volume can be easily established to about 20% accuracy with techniques known to those of skill in the art. Preferably, techniques with relatively improved accuracy such as but not limited to spirometry are used. Accordingly, the instant invention provides a clinically useful real-time blood measurement tool.

Further, and advantageously, MR spectroscopy using $^{129}$Xe can be simpler and less expensive relative to the cost of other MR images. For example, the quantity of polarized gas needed, the polarization level of the polarized gas, and the isotopic enrichment can be reduced as compared to those used for conventional polarized gas MR imaging. In one embodiment, the spectroscopic perfusion measurement can be made with about 100 cc of unenriched gas polarized to only 1–2%. This is in comparison to a polarization of 20% for 500 cc of 80% isotopically enriched $^{129}$Xe to yield a comparable MR image. Still another advantage is that the spectroscopic methods do not require a polarization calibration because the measurement is "self-calibrating". Stated differently, the polarization is cancelled by comparing dissolved and gaseous xenon signal, both of which can be assumed to have identical polarization to the extent that T1 relaxation in the blood is negligible, which it is for short $T_R$ settings as discussed above. Other advantages include the use of low magnetic field systems, such as 0.1–1.0 Tesla, and preferably about 0.075–0.2 T, and more preferably about 0.1–0.15 T. The lower field limit is established by the length of the pulse needed to get selective excitation. For example, a 200 ppm shift at 1.5 T means a frequency difference of about 3.52 kHz. Thus, for a hard pulse, it is desired to have a pulse length of about 284 μs so that the gas phase remains substantially or totally unexcited. Reducing the field by a factor often to 0.15 T gives a frequency difference of 0.352 KHz and the corresponding discriminating pulse length of about 2.84 ms. Similarly, at 0.015 T (150 G), the pulse length is relatively long (28 ms). The longer pulse time at this field strength T2 can potentially degrade the signal because T2 can dephase the signal before the pulse application is complete.

Advantageously, the method can be used successfully in systems having relatively poor magnet homogeneity because the field gradients do not adversely impact the spectroscopy perfusion method. By eliminating the necessity for these items, system operating costs can potentially be greatly reduced.

Further, a simplified and lower cost polarizer system can be used to polarize the $^{129}$Xe for this method. For example, the low cost polarizer system can use a lower power optical laser (such as a 10 Watt laser) and reduced accuracy measurement and associated equipment attributed to the elimination of the need for accurate polarization, each of which can provide additional cost savings over that of other systems used for other imaging methods.

Preferably, the appropriate magnet homogeneity associated with a patient's chest area for the spectroscopy imaging method of the instant invention is estimated by the corresponding chemical shift of $^{129}$Xe in the dissolved phase in the blood over that in the gaseous phase. This shift, as discussed above, is about 200 ppm. Thus, in order to achieve "selective" excitation of the dissolved phase, a field homogeneity of about 50 ppm or better is preferred. More preferably, a field homogeneity of about 20 ppm or better is used. In contrast, conventional MRI systems are shimmed to about 1 ppm to operate with about a 1 ppm homogeneity. The lower limit of the magnetic field strength used in the spectroscopy method of the instant invention can be determined by the pulse time used to selectively excite the dissolved phase (instead of the gas phase). The frequency difference ("$\Delta v$") between the gas and dissolved phase can stated by:

$$\Delta v = \frac{\gamma}{2\pi} \delta B_0. \quad (16)$$

Wherein $B_0$ is the strength of the magnetic field, $\gamma$ is the gyromagnetic ratio of $^{129}$Xe and $\delta$ is the chemical shift separating the gas and dissolved phases. Accordingly, when applying a pulse which selectively excites one phase rather than the other, the length of the pulse should be sufficiently long to have a sufficiently narrow frequency bandwidth. For example, by Fourier analysis, a square excitation pulse of duration $t_{rf}$ will have an frequency spectrum centered on the pulse frequency with a frequency width ("$\Delta v_{rf}$") of about $1/t_{rf}$. Thus, for phase discrimination, the pulse frequency distribution width is preferably smaller than the frequency separation between the phases ($\Delta v_{rf} < \Delta v$). Thus, the approximate lower field limit can be written as:

$$B_0 \geq \frac{2\pi}{\gamma \delta t_{rf}}. \quad (17)$$

Although the pulse time $t_{rf}$ can be as long as necessary to achieve dissolved phase discrimination at the given field strength, the pulse length time is also limited by the timescale of the blood flow effects ($t_p$) as well as T2 and T2*. Preferably, a large number of pulses are generated during the time interval ($t_p$). Preferably, at least 25 excitation pulses are applied during this interval, more preferably at least 50, and most preferably about 100 pulses. Assuming the time scale is about 2.5 seconds, as discussed above, then a preferable pulse time ($t_{rf}$) is about 25 ms. For $\gamma = 7402 G^{-1} s^{-1}$, an exemplary minimum field strength is about 170 gauss ("G"). This is a relatively low field, approximately $1/100$ the standard 1.5 T imaging magnet.

Figure 6:
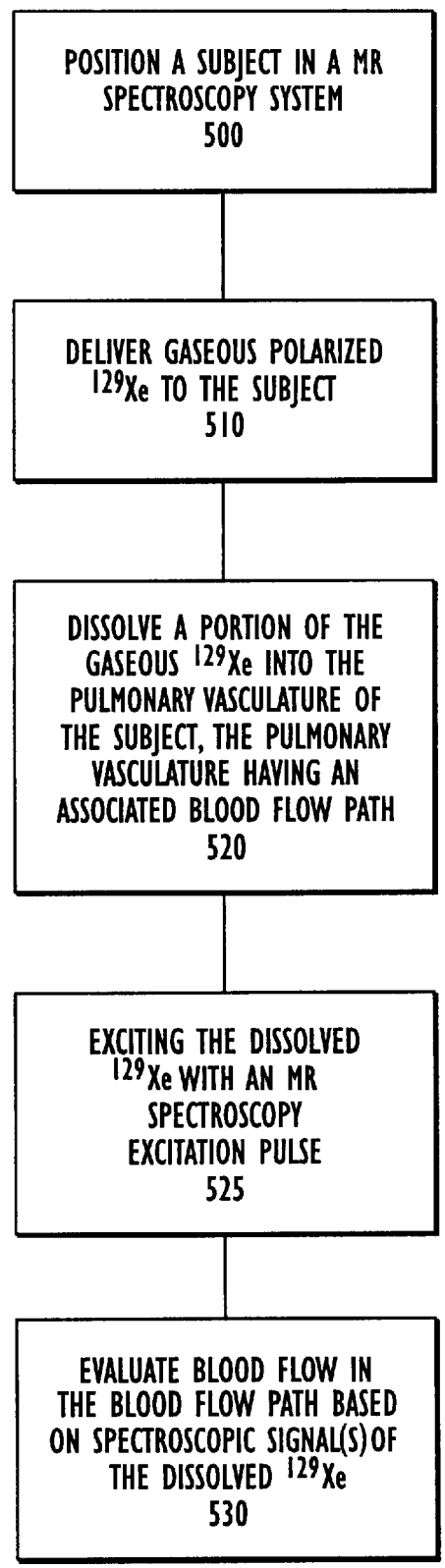
FIG. 6 is a flow chart illustrating one embodiment of a method for spectroscopic imaging according to the present invention.

In an additional embodiment of the spectroscopic blood flow method of the instant invention, pulmonary emboli or other blockage can be detected by measuring the pulmonary blood flow rate (Q). This measurement is based on normal blood flow rates in healthy subjects. Preferably, the blockage detection method also considers heart rate. In a preferred embodiment, the detection method correlates the blood flow rate (Q) with heart rate ("R"). For example, the detection method preferably uses a normalized flow rate Q/R. Thus, as illustrated by FIG. 6, the detection method includes positioning a subject in a MR spectroscopy unit (Block 500) and delivering gaseous polarized $^{129}$Xe to the subject (Block 510). A portion of the gaseous $^{129}$Xe is dissolved into the pulmonary vasculature which has an associated perfusion or pulmonary blood flow path (Block 520). The blood flow is evaluated based on the spectroscopy signal of the dissolved $^{129}$Xe (Block 530). This method can yield unique real-time information about blood flow and perfusion that is difficult to achieve by other means. In a preferred embodiment, the dissolved phase $^{129}$Xe is (selectively) excited with a large flip angle excitation pulse as described above (Block 525). It is also preferred that the pulse sequence be correlated with the blood volume (or flow rate) to maximize the signal with the magnetization in the blood.

Preferably, the method includes detecting blockage in the blood flow path of the subject based on the results of the measuring step. In one embodiment, the blood flow rates of healthy subjects are compared to the measured flow rate to perform the detecting step. In determining if there is a problem, the heart rate is taken into account. Accordingly, in a preferred embodiment, the method uses the heart rate of the subject to normalize the measured blood flow rate.

Advantageously, for repetition times ($T_R$) which are less than $t_p$, the signal will be substantially linear with $T_R$. In addition, an integrated signal versus $T_R$ will be proportional to blood flow rate (Q). Thus, a substantially calibrated measurement of the blood flow rate (Q) can advantageously be obtained. This can be done relatively inexpensively with a low field magnet and with low homogeneity requirements. Advantageously, such a calibration can be performed accurately and relatively simply.

In another preferred embodiment, a spectroscopic signal associated with the dissolved-phase $^{129}$Xe can be derived such that it represents a blood volume or blood flow rate. The patient can then be subjected to a drug therapy or surgery to treat a cardiac or pulmonary vasculature or blood flow problem. A second signal can then be obtained and a comparative, relative, or percent increase (or decrease) in blood flow can be obtained without requiring an "absolute value" of blood volume. Such a comparative MR spectroscopy evaluation can be done in real-time to indicate during surgery (such as during angioplasty) whether a blood flow path obstruction has been removed or diminished. Further, such a comparative measurement or evaluation can be used to determine whether drug therapy improved a patient's blood flow (by allowing an increased blood volume or rate (such as due to a less viscous blood or lipid management) and the like.

Additionally, due to the depolarizing effect of oxygen depleted blood on dissolved phase polarized $^{129}$Xe, MR spectroscopy signal intensity (reduced or increased) can be used to evaluate conditions associated with reduced or increased levels of oxygen along the xenon-blood barrier or blood flow path. The deoxyhemoglobin is paramagnetic and has a greater depolarizing effect on the dissolved phase $^{129}$Xe. The well oxygenated blood or tissue provide longer T1's compared to oxygen starved blood or tissue. Thus, a stronger spectroscopy signal relates to well oxygenated levels of oxygen in the tissue or blood while a weaker or lower spectroscopic polarization-based signal relates to oxygen-starved, depleted or deprived regions.

OTHER EMBODIMENTS

The present invention has been described above with respect to particular preferred embodiments. Those skilled in the art, however, will appreciate that the invention can be employed for a broad range of applications. Methods for imaging or obtaining information about blood flow using dissolved hyperpolarized $^{129}$Xe can be carried out according to the present invention using magnetic resonance or spectroscopic techniques known to those skilled in the art. See, e.g., U.S. Pat. No. 5,833,947; U.S. Pat. No. 5,522,390; U.S. Pat. No. 5,509,412, U.S. Pat. No. 5,494,655, U.S. Pat. No. 5,352,979; and U.S. Pat. No. 5,190,744. See also Hou et al., *Optimization of Fast Acquisition Methods for Whole-Brain Relative Cerebral Blood Volume (rCBV) Mapping with Susceptibility Contrast Agents,* 9 J. Magnetic Resonance Imaging 233 (1999); Simonsen et al., *CBF and CBV Measurements by USPIO Bolus Tracking: Reproducibility and Comparison with Gd-Based Values,* 9 J. Magnetic Resonance Imaging 342 (1999); Mugler III et al., *MR Imaging and Spectroscopy Using Hyperpolarized $^{129}$Xe gas: Preliminary Human Results,* 37 Magnetic Resonance in Medicine, pp. 809–815 (1997); Belliveau et al., *Functional Cerebral Imaging by Susceptibility-Contrast NMR,* 14 Magnetic Resonance in Medicine 14 538 (1990); Detre et al., *Measurement of Regional Cerebral Blood Flow in Cat Brain Using Intracarotid $^2H_2O$ and $^2H$ NMR Imaging,* 14 Magnetic Resonance in Medicine 389 (1990); Frank et al., *Dynamic Dysprosium-DTPA-BMA Enhanced MRI of the Occipital Cortex; Functional Imaging in Visually Impaired Monkeys by PET and MRI* (Abstract), Ninth Annual Scientific Meeting and Exhibition of the Society of Magnetic Resonance In Medicine (Aug. 18–24, 1990); Le Bihan, *Magnetic Resonance Imaging of Perfusion,* 14 Magnetic Resonance in Medicine 283 (1990); and Rosen et al., *Perfusion Imaging by Nuclear Magnetic Resonance,* 5 Magnetic Resonance Quarterly 263 (1989). The contents of these documents are hereby incorporated by reference as if recited in full herein.

In particular embodiments, the present invention can be practiced to give a quantitative assessment of blood flow (more preferably, perfusion) as will be appreciated by one of skill in the art. According to this embodiment, signal intensity can be followed over time, and the area under the resulting curve can be integrated to give a quantitative measure of blood flow. Examples of such quantitative relationships were developed for use with radioactive contrast agents with MR imaging and spectroscopy methods may be particularly suitable for dissolved phase $^{129}$Xe analysis of blood vessels. See, generally, Lassen, *Cerebral Transit of an Intravascular Tracer may Allow Measurement of regional Blood Volume but not Regional Blood Flow,* 4 J. Cereb. Blood Flow and Metab. 633 (1984). However, it will be appreciated by one of skill in the art, that, unlike the radioactive contrast agents, the polarized states of both the gas and the dissolved phase gas (in the body of a subject) are relatively short and "automatically" terminate within the body within blood within less than about 1–2 minutes (depending on the polarization level) from the time when the inhalation procedure or gaseous supply is terminated at the lungs. Therefore, after about 1 minute, there is typically no "residue" polarized gas to image or to generate an MR detectable signal to potentially interfere with MR signal evaluations.

Furthermore, the inventive methods may be used for wide range of diagnostic and evaluative applications, preferably those related to cardiac, pulmonary or cardiovascular function, as described in more detail below.

In preferred embodiments, the inventive methods are used to determine perfusion rates (e.g., absolute and/or relative perfusion), and more preferably to identify and/or assess the severity of abnormal perfusion. In other particular embodiments, temporal variations in blood flow are determined, e.g., to assess the effects of a vasocontractory or vasodilatory substance and/or to identify regions of surgically induced variations in blood perfusion.

Other applications of the present invention include, but are not limited to: identification and assessment of the presence or absence and/or severity of cardiac ischemias and/or infarcts; localization and assessment of thrombi and plaques; determination of "therapeutic windows" for administering heparin, vasodilators, antihypertensive agents, calcium antagonists and the like, e.g., in reversible focal ischemia; monitoring of other induced vasodilator effects; detection and quantitative evaluation of the severity of ischemias; monitoring the vasodilatory or vasocontractory effects of a physiologically active substance; and monitoring surgically induced blood perfusion variations.

The present invention may further be employed for: assessment of cerebral perfusion in following induced subarachnoid hemorrhage or in conditions marked by brain dysfunction, e.g., in connection with acute severe symptomatic hyponatremia; evaluation of new therapies, e.g., in the treatment of cerebral vasospasm (including but not limited to, anti-thrombolytic therapies, calcium channel blockers, anti-inflammatory therapies, angioplasty, and the like); assessment of the presence or absence and/or severity of ischemia in large tissue masses; assessment of the relationship between blood metabolites and cerebral perfusion in cerebral ischemia associated with acute liver failure, e.g., for the treatment of Alzheimer's disease; evaluation of new therapies for stroke, including but not limited to, t-PA, aspirin antiphospholipids, lupus anticoagulants, antiphospholipid antibodies, and the like; evaluation of risk factors for stroke, e.g., serum lipid levels; evaluation of induced brain hypothermia on cerebral perfusion during neurosurgery, e.g., for stroke; evaluation of the effects of age on cerebral perfusion, e.g., to study lacunar infarcts; and assessment of narcotics, e.g., cocaine, amphetamines, ethanol, and the like, on the ischemic brain.

The present invention finds use for both veterinary and medical applications. The present invention may be advantageously employed for diagnostic evaluation and/or treatment of subjects, in particular human subjects, because it may be safer (e.g., less toxic) than other methods known in the art (e.g., radioactive methods). In general, the inventive methods will be more readily accepted because they avoid radioactivity or toxic levels of chemicals or other agents. Subjects according to the present invention can be any animal subject, and are preferably mammalian subjects (e.g., humans, canines, felines, bovines, caprines, ovines, equines, rodents, porcines, and/or lagomorphs), and more preferably are human subjects.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. In the claims, means-plus-function clause are intended to cover the structures described herein as performing the recited function and not only structural equivalents but also equivalent structures. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed is:

1. A method for MRI imaging the pulmonary and/or cardiac vasculature using dissolved-phase polarized $^{129}$Xe, comprising the steps of:

delivering polarized $^{129}$Xe gas to a predetermined region of the patient's body, the polarized gas having a dissolved imaging phase associated therewith;

exciting a predetermined region of the patient's body having a portion of the dissolved phase polarized gas therein with at least one large flip angle RF excitation pulse;

acquiring at least one MR image associated with the dissolved phase polarized gas after said exciting step, wherein said delivering step includes having the patient inhale the polarized $^{129}$Xe gas into the lungs, the polarized $^{129}$Xe having a gas phase resonance which is higher than the dissolved-phase resonance, and wherein at least a portion of the polarized $^{129}$Xe gas enters into the pulmonary vasculature in a dissolved-phase, and wherein at least a portion of the dissolved-phase polarized $^{129}$Xe then enters the blood stream with an associated perfusion rate wherein a differential MRI image is obtained which comprising data associated with the physiology of the lungs of the patient, the physiology of the vasculature of the patient, blood flow in the patient, and perfusion in the patient, the data corresponding to both the $^{129}$Xe gas and dissolved-gas phase, and wherein said differential image is obtained by exciting the $^{129}$Xe gas phase with an RF pulse having an excitation pulse frequency which corresponds to the resonance of the gas phase and exciting the dissolved phase with an RF pulse having an excitation frequency which corresponds to the resonance of the dissolved phase, and wherein the gas phase RF excitation pulse is a small flip angle pulse and the dissolved phase RF excitation pulse is a large flip angle pulse.

2. A method for MRI imaging the pulmonary and/or cardiac vasculature using dissolved-phase polarized $^{129}$Xe, comprising the steps of:

delivering polarized $^{129}$Xe gas to a predetermined region of the patient's body, the polarized gas having a dissolved imaging phase associated therewith;

exciting a predetermined region of the patient's body having a portion of the dissolved phase polarized gas therein with at least one large flip angle RF excitation pulse;

acquiring at least one MR image associated with the dissolved phase polarized gas after said exciting step, wherein said delivering step comprises having the patient inhale the polarized $^{129}$Xe gas into the lungs, the polarized $^{129}$Xe having a gas phase resonance which is higher than the dissolved-phase resonance, and wherein at least a portion of the polarized $^{129}$Xe gas enters into the pulmonary vasculature in a dissolved-phase, and wherein at least a portion of the dissolved-phase polarized $^{129}$Xe then enters the blood stream with an associated perfusion rate; and delivering via inhalation a quantity of polarized $^3$He gas, and wherein a MRI differential image is obtained comprising data corresponding to the polarized gas $^3$He in the lungs in addition to the dissolved phase polarized $^{129}$Xe.

3. A method for MRI imaging the pulmonary and/or cardiac vasculature using dissolved-phase polarized $^{129}$Xe, comprising the steps of:

delivering polarized $^{129}$Xe gas to a predetermined region of the patient's body, the polarized gas having a dissolved imaging phase associated therewith;

exciting a predetermined region of the patient's body having a portion of the dissolved phase polarized gas therein with at least one large flip angle RF excitation pulse; and acquiring at least one MR image associated with the dissolved phase polarized gas after said exciting step, wherein said exciting step is repeated within a predetermined repetition time, the predetermined repetition time being less than the time it takes for a given volume of blood to move from the lungs to the heart, wherein said delivering step comprises inhalation of the polarized $^{129}$Xe gas into the lungs, the $^{129}$Xe having a gas phase resonance which is higher than the dissolved-phase resonance, wherein at least a portion of the polarized $^{129}$Xe gas enters into the pulmonary vasculature in a dissolved-phase, wherein at least a portion of the dissolved-phase polarized $^{129}$Xe then enters the blood stream with an associated perfusion rate and wherein said inhalation delivering step comprises a breath-hold delivery period.

4. A method according to claim 3, wherein the breath-hold period is at least 10 seconds.

5. A method according to claim 1, wherein the at least one image is a multi-echo image.

6. A method according to claim 5, wherein the multi-echo image is one of a slice selective and volume selective image pattern.

7. A method for MRI imaging the pulmonary and/or cardiac vasculature using dissolved-phase polarized $^{129}$Xe, comprising the steps of:

delivering polarized $^{129}$Xe gas to a predetermined region of the patient's body, the polarized gas having a dissolved imaging phase associated therewith;

exciting a predetermined region of the patient's body having a portion of the dissolved phase polarized gas therein with at least one large flip angle RF excitation pulse; and acquiring at least one MR image associated with the dissolved phase polarized gas after said exciting step, wherein said exciting step is repeated within a predetermined repetition time, the predetermined repetition time being less than the time it takes for a given volume of blood to move from the lungs to the heart, wherein said delivering step comprises inhalation of the polarized $^{129}$Xe gas into the lungs, the $^{129}$Xe having a gas phase resonance which is higher than the dissolved-phase resonance, wherein at least a portion of the polarized $^{129}$Xe gas enters into the pulmonary vasculature in a dissolved-phase, wherein at least a portion of the dissolved-phase polarized $^{129}$Xe then enters the blood stream with an associated perfusion rate, and wherein the repetition time is decreased to emphasize a signal associated with capillaries in the pulmonary region.

8. A method for MRI imaging the pulmonary and/or cardiac vasculature using dissolved-phase polarized $^{129}$Xe, comprising the steps of:

delivering polarized $^{129}$Xe gas to a predetermined region of the patient's body, the polarized gas having a dissolved imaging phase associated therewith;

exciting a predetermined region of the patient's body having a portion of the dissolved phase polarized gas therein with at least one large flip angle RF excitation pulse; and acquiring at least one MR image associated with the dissolved phase polarized gas after said exciting step, wherein said exciting step is repeated within a predetermined repetition time, the predetermined repetition time being less than the time it takes for a given volume of blood to move from the lungs to the heart, wherein said delivering step comprises inhalation of the polarized $^{129}$Xe gas into the lungs, the $^{129}$Xe having a gas phase resonance which is higher than the dissolved-phase resonance, wherein at least a portion of the polarized $^{129}$Xe gas enters into the pulmonary vasculature in a dissolved-phase, wherein at least a portion of the dissolved-phase polarized $^{129}$Xe then enters the blood stream with an associated perfusion rate, and wherein the repetition time is increased to include distal vasculature relative to the pulmonary capillaries.

9. A method for MRI imaging the pulmonary and/or cardiac vasculature using dissolved-phase polarized 129Xe, comprising the steps of:

delivering polarized $^{129}$Xe gas to a predetermined region of the patient's body, the polarized gas having a dissolved imaging phase associated therewith;

exciting a predetermined region of the patient's body having a portion of the dissolved phase polarized gas therein with at least one large flip angle RF excitation pulse; and acquiring at least one MR image associated with the dissolved phase polarized gas after said exciting step, wherein said exciting step is repeated within a predetermined repetition time, the predetermined repetition time being less than the time it takes for a given volume of blood to move from the lungs to the heart, wherein dissolved-phase $^{129}$Xe has an associated decay time constant (T1) corresponding to its polarization life and a transverse relaxation time in blood ($T_2^*$), and wherein for $T_2^*$ greater than about 100 ms, said acquiring step employs one of EPI and RARE multi-echo imaging methods.

10. A method according to claim 8, wherein said acquiring step acquires at least 32 echoes per each excitation pulse.

11. A method for MRI imaging the pulmonary and/or cardiac vasculature using dissolved-phase polarized $^{129}$Xe, comprising the steps of:

delivering polarized $^{29}$Xe gas to a predetermined region of the patient's body, the polarized gas having a dissolved imaging phase associated therewith;

exciting a predetermined region of the patient's body having a portion of the dissolved phase polarized gas therein with at least one large flip angle RF excitation pulse; and acquiring at least one MR image associated with the dissolved phase polarized gas after said exciting step, wherein said exciting step is repeated within a predetermined repetition time, the predetermined repetition time being less than the time it takes for a given volume of blood to move from the lungs to the heart, and wherein cardiac gating is used so that said acquiring step is timed such that it is performed during slow blood flow periods.

12. A method for MRI imaging the pulmonary and/or cardiac vasculature using dissolved-phase polarized $^{129}$Xe, comprising the steps of:

delivering polarized $^{129}$Xe gas to a predetermined region of the patient's body, the polarized gas having a dissolved imaging phase associated therewith;

exciting a predetermined region of the patient's body having a portion of the dissolved phase polarized gas therein with at least one large flip angle RF excitation pulse; and acquiring at least one MR image associated with the dissolved phase polarized gas after said exciting step, wherein said exciting step is repeated within a predetermined repetition time, the predetermined repetition time being less than the time it takes for a given volume of blood to move from the lungs to the heart, wherein said delivering step comprises inhalation of the polarized $^{129}$Xe gas into the lungs, the $^{129}$Xe having a gas phase resonance which is higher than the dissolved-phase resonance, wherein at least a portion of the polarized $^{129}$Xe gas enters into the pulmonary vasculature in a dissolved-phase, wherein at least a portion of the dissolved-phase polarized $^{129}$Xe then enters the blood stream with an associated perfusion rate, wherein the at least one image is a multi-echo image, and wherein the multi-echo imaging uses one of gradient recalled and RF recalled echoes.

13. A method for evaluating the blood flow of a patient, comprising the steps of:

positioning a subject in a MR spectroscopy system capable of detecting spectroscopic signals in a subject having a pulmonary vasculature;

delivering gaseous polarized $^{129}$Xe to the subject;

dissolving a portion of the gaseous polarized $^{129}$Xe into the pulmonary vasculature having an associated blood flow path;

exciting the dissolved portion of the $^{129}$Xe with an MR spectroscopy RF excitation pulse; and evaluating blood flow of the patient based on a spectroscopic signal corresponding to the dissolved polarized $^{129}$Xe, wherein said evaluating step includes the step of exciting the dissolved $^{129}$Xe with a large angle RF excitation pulse, wherein the MR Spectroscopy System comprises a magnetic field operably associated therewith, and wherein the magnetic field strength is less than about 0.5 T.

14. A method according to claim 13, wherein said evaluating step is performed to provide real-time blood flow information.

15. A method for quantitatively evaluating the blood flow rate of a subject, comprising the steps of:

administering gaseous polarized $^{129}$Xe to a subject such that the gaseous polarized $^{129}$Xe enters the subject's lungs;

transmitting at least one large flip angle RF excitation pulse to the $^{129}$Xe after it travels, dissolved, into the subject's vasculature based on said administering step;

obtaining a first polarized dissolved $^{129}$Xe spectroscopic response signal based on said large flip angle pulse transmitting step, the first response signal having a signal strength associated therewith;

obtaining a second polarized dissolved $^{129}$Xe spectroscopic response signal based on said at least one large flip angle pulse transmitting step, the second response signal having a signal strength associated therewith, wherein said second polarized dissolved $^{129}$Xe response signal obtaining step is temporally spaced apart a time interval from said first dissolved response signal obtaining step;

monitoring the increase in signal strength of the dissolved polarized $^{129}$Xe response signal over time based on said first and second dissolved response signal obtaining steps;

transmitting a predetermined flip angle RF excitation pulse to the gaseous $^{129}$Xe residing in the lung void space based on said administering step;

obtaining a first polarized $^{129}$Xe gas spectroscopic response signal based on said predetermined flip angle gaseous excitation transmitting step;

comparing the polarized $^{129}$Xe gas response signal with the first and second dissolved polarized $^{129}$Xe response signals; and evaluating the blood flow rate of the subject based on said comparing step.

16. A method according to claim 15, further comprising the step of quantitatively determining the blood flow rate of the subject based on said comparing step.

17. A method according to claim 15, further comprising obtaining a third polarized dissolved $^{129}$Xe spectroscopic response signal based on said at least one large flip angle pulse transmitting step, the third response signal having a signal strength associated therewith, wherein said third dissolved response signal obtaining step is temporally spaced apart a time interval from said first and second dissolved response signal obtaining steps.

18. A method according to claim 16, wherein said at least one large flip angle transmitting step comprises transmitting two temporally separate large flip angle pulses.

19. A method according to claim 16, further comprising the step of calculating the slope of a line corresponding to the dissolved $^{129}$Xe response signal intensity over pulse repetition time.

20. A method according to claim 19, further comprising the step of mathematically dividing the slope with the value of the $^{129}$Xe gas response signal generated in said gas response signal obtaining step.

21. A method according to claim 16, further comprising the step of numerically fitting a line to the signal strength of the first and second dissolved $^{129}$Xe response signals to calculate the slope of the line corresponding to the dissolved $^{129}$Xe response signals.

22. A method according to claim 15, further comprising the step of generating a Magnetic Resonance image of the polarized $^{129}$Xe in the lungs of the subject subsequent to said administering step.

23. A method according to claim 15, further comprising the step of administering a physiologically active medication to a subject and evaluating its affect on the blood flow rate of a subject.

24. A method according to claim 16, further comprising the step of determining a lung volume representative of the subject's lungs and using the determined lung volume in said quantitative determination step.

25. A method according to claim 16, further comprising the step of normalizing the blood flow rate obtained in said determining step by considering the subject's heart rate.

26. A method according to claim 15, further comprising the step of evaluating the existence of perfusion deficiencies or abnormalities.

27. A method according to claim 26, wherein said evaluating step is carried out by monitoring the intensity of the dissolved polarized $^{129}$Xe response signal over time to obtain diagnostic information.

28. A method according to claim 27, wherein said evaluating step includes assessing cerebral perfusion.

29. A method for quantitatively evaluating the blood flow rate of a subject, comprising the steps of:

administering gaseous polarized $^{129}$Xe to a subject such that the gaseous polarized $^{129}$Xe enters the subject's lungs;

transmitting at least one large flip angle RF excitation pulse to the $^{129}$Xe after it travels, dissolved, into the subject's vasculature based on said administering step;

obtaining a first polarized dissolved $^{129}$Xe spectroscopic response signal based on said large flip angle pulse transmitting step, the first response signal having a signal strength associated therewith;

obtaining a second polarized dissolved $^{129}$Xe spectroscopic response signal based on said at least one large flip angle pulse transmitting step, the second response signal having a signal strength associated therewith, wherein said second dissolved polarized $^{129}$Xe response signal obtaining step is temporally spaced apart a time interval from said first dissolved polarized $^{129}$Xe response signal obtaining step;

monitoring the increase in signal strength of the dissolved polarized $^{129}$Xe response signal over time based on said first and second dissolved response signal obtaining steps; and evaluating the blood flow rate of the subject based on said monitoring step.

30. A method according to claim 29, further comprising the steps of administering a medication to the subject and monitoring the efficacy of the medication based on said evaluating blood flow rate step.

31. A method according to claim 29, wherein said evaluating step comprises the steps of:

transmitting a predetermined flip angle RF excitation pulse to the gaseous $^{129}$Xe residing in the lung void space based on said administering step;

obtaining a first polarized $^{129}$Xe gas spectroscopic response signal having an associated signal strength based on said predetermined flip angle gaseous excitation transmitting step;

comparing the polarized $^{129}$Xe gas phase response signal with the first and second dissolved $^{129}$Xe response signals; and quantitatively determining the blood flow rate of the subject based on said comparing step.

32. A method according to claim 29, further comprising the step of calculating the slope of a line corresponding to the dissolved polarized $^{129}$Xe signal intensity over pulse repetition time.

33. A method according to claim 31, further comprising the step of mathematically dividing the slope with the value of the polarized $^{129}$Xe gas response signal strength generated in said gas phase obtaining step.

34. A method according to claim 29, further comprising the step of generating a Magnetic Resonance image of the polarized $^{129}$Xe in the lungs of the subject subsequent to said administering step.

35. A method according to claim 31, further comprising the step of identifying a lung volume representative of the subject's lungs and using the identified lung volume in said blood flow rate determination step.

36. A method according to claim 31, further comprising the step of normalizing the blood flow rate obtained in said determining step by taking into account the subject's heart rate.

37. A method according to claim 29, further comprising the step of evaluating the existence of perfusion deficiencies or abnormalities.

38. A method for quantitatively evaluating perfusion abnormalities and/or the blood flow rate of a subject, comprising the steps of:

administering gaseous polarized $^{129}$Xe to a subject such that the gaseous polarized $^{129}$Xe enters the subject's lungs;

transmitting at least one large flip angle RF excitation pulse to the $^{129}$Xe after it travels, dissolved, into the subject's vasculature based on said administering step;

obtaining a first polarized dissolved $^{129}$Xe spectroscopic response signal based on said large flip angle pulse transmitting step, the first response signal having a signal strength associated therewith;

obtaining a second polarized dissolved $^{129}$Xe spectroscopic response signal based on said at least one large flip angle pulse transmitting step, the second response signal having a signal strength associated therewith, wherein said second dissolved polarized $^{129}$Xe response signal obtaining step is temporally spaced apart a time interval from said first dissolved polarized $^{129}$Xe obtaining step;

monitoring the signal strength of the dissolved polarized $^{129}$Xe response signal over time based on said first and second dissolved polarized $^{129}$Xe response signal obtaining steps; and evaluating at least one of perfusion function or blood flow in the blood flow path of the subject based on said monitoring step.

39. A method according to claim 38, wherein said evaluating step comprises assessing at least one of (a) perfusion deficits in the pulmonary vasculature or the cardiac vasculature, (b) pulmonary vasculature emboli, (c) blood flow related circulatory system deficits, and (d) restrictions and obstructions in the blood flow path of the subject.

40. A method according to claim 38, wherein said evaluating step is carried out by monitoring the intensity of the dissolved polarized $^{129}$Xe response signal over time to obtain diagnostic information.

41. A method according to claim 40, wherein said evaluating step comprises assessing cerebral perfusion.

42. A method according to claim 40, wherein said evaluating step comprises assessing blood flow path blockage or restrictions.

43. A method according to claim 38, wherein said evaluating step comprises one or more of:

(a) identifying the presence or absence of cardiac ischemias or infarcts;

(b) identifying thrombi or plaques;

(c) determining therapeutic windows for administering heparin, vasodilators, antihypertensive agents, and calcium antagonists;

(d) evaluating the severity or existence of ischemias;

(e) evaluating therapies in the treatment of cerebral vasospasm;

(f) assessing ischemia in large tissue masses;

(g) assessing the relationship between blood metabolites and cerebral perfusion in cerebral ischemia for the diagnosis or treatment of Alzheimer's disease;

(h) evaluating therapies for stroke, (i) evaluating risk factors for stroke (j) evaluating induced brain hypothermia on cerebral perfusion during neurosurgery for stroke (k) evaluating the effects of age on cerebral perfusion; and (l) assessing the effect of narcotics, on the ischemic brain.

44. A method for MRI imaging the pulmonary and/or cardiac vasculature using polarized $^{129}$Xe dissolved in the blood stream, comprising the steps of:

administering gaseous polarized $^{129}$Xe to a subject such that the gaseous polarized $^{129}$Xe enters the subject's lungs;

transmitting at least one large flip angle RF excitation pulse from an MR apparatus to a first quantity of the $^{129}$Xe after it travels, dissolved, into the subject's vasculature based on said administering step;

substantially destroying the polarization of the $^{129}$Xe dissolved in the subject's vasculature based on said first transmitting step;

delaying a predetermined period of time and then transmitting a second large flip angle RF excitation pulse from the MR apparatus to a second quantity of the $^{129}$Xe after it travels, dissolved, into the subject's vasculature, wherein the predetermined time is sufficient to allow the uptake of the second quantity of polarized $^{129}$Xe into the vasculature based on said administering step;

obtaining first and second response signals for the polarized dissolved $^{129}$Xe based on the corresponding first and second transmitting steps, the first and second response signals each having a signal strength associated therewith;

transmitting a third RF excitation pulse from the MR apparatus to excite the $^{129}$Xe gas in the lung of the subject;

obtaining a third response signal corresponding to the third transmitting step; and acquiring at least one MR image comprising data provided by said first and second obtaining steps associated with the dissolved polarized $^{129}$Xe in the vasculature and at least one MR image comprising data provided by said third obtaining step associated with the $^{129}$Xe in the lung, wherein the predetermined time between said first and second transmitting steps is defined as a pulse repetition time, wherein said pulse repetition time is less than about 3 seconds, and wherein the first, second, and third obtaining steps are carried out during a single imaging session.

45. A method according to claim 44, wherein said at least one image is a differential MRI image comprising data corresponding to both the polarized $^{129}$Xe gas in the lungs and the polarized dissolved $^{129}$Xe in the vasculature.

46. A method according to claim 44, wherein the at least one image is a multi-echo image, and wherein the multi-echo imaging uses one of gradient recalled and RF recalled echoes.

47. A method according to claim 44, wherein the pulse repetition time is decreased to emphasize a signal associated with capillaries in the pulmonary region.

48. A method according to claim 44, wherein the pulse repetition time is increased to include distal vasculature relative to the pulmonary capillaries.

49. A method according to claim 44, wherein dissolved-phase $^{129}$Xe has an associated decay time constant (T1) corresponding to its polarization life and a transverse relaxation time in blood ($T_2^*$) greater than about 100 ms and said acquiring step employs one of EPI and RARE multi-echo imaging methods.

50. A method according to claim 44, wherein cardiac gating is used so that said acquiring step is timed such that it is performed during slow blood flow periods.

51. A method according to claim 44, wherein said method further comprising the step of providing a cardiac coil which is positioned proximate to the cardiac region of the subject, the cardiac coil being configured to spatially limit the excitation pulses transmitted to the subject.

52. A method according to claim 44, wherein the MR image of the dissolved polarized $^{129}$Xe MR image and the MR image of the polarized $^{129}$Xe gas in the lung are obtained during a single breath-hold inhalation cycle.

\* \* \* \* \*

UNITED STATES PATENT AND TRADEMARK OFFICE
CERTIFICATE OF CORRECTION

PATENT NO.    : 6,346,229 B1
DATED         : February 12, 2002
INVENTOR(S)   : Driehuys et al.

It is certified that error appears in the above-identified patent and that said Letters Patent is hereby corrected as shown below:

Column 26,
Line 61, "$^{29}$Xe" should read -- $^{129}$Xe --

Signed and Sealed this

First Day of April, 2003

JAMES E. ROGAN
*Director of the United States Patent and Trademark Office*

UNITED STATES PATENT AND TRADEMARK OFFICE
CERTIFICATE OF CORRECTION

| | | |
|---|---|---|
| PATENT NO. | : 6,346,229 B1 | Page 1 of 1 |
| APPLICATION NO. | : 09/271476 | |
| DATED | : February 12, 2002 | |
| INVENTOR(S) | : Driehuys et al. | |

It is certified that error appears in the above-identified patent and that said Letters Patent is hereby corrected as shown below:

Claim 11, Page 26, Column 2, Line 61, "$^{29}$Xe" should read --$^{129}$Xe--

Claim 13, Page 27, Column 1, Line 53 "includes" should read --comprises--

Claim 14, Page 27, Column 1, Line 62 "information" should read --data--.

Signed and Sealed this

Tenth Day of July, 2007

JON W. DUDAS
*Director of the United States Patent and Trademark Office*